(12) United States Patent
Lorenz et al.

(10) Patent No.: US 7,010,336 B2
(45) Date of Patent: Mar. 7, 2006

(54) MEASUREMENT SITE DEPENDENT DATA PREPROCESSING METHOD FOR ROBUST CALIBRATION AND PREDICTION

(75) Inventors: Alexander D. Lorenz, Chandler, AZ (US); Timothy L. Ruchti, Gilbert, AZ (US); Thomas B. Blank, Chandler, AZ (US); Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 259 days.

(21) Appl. No.: 10/384,023

(22) Filed: Mar. 7, 2003

(65) Prior Publication Data

US 2003/0216627 A1 Nov. 20, 2003

Related U.S. Application Data

(63) Continuation-in-part of application No. 09/630,201, filed on Aug. 1, 2000, now Pat. No. 6,871,169, which is a continuation-in-part of application No. 09/610,789, filed on Jul. 6, 2000, now abandoned, which is a continuation-in-part of application No. 08/911,588, filed on Aug. 14, 1997, now Pat. No. 6,115,673.

(60) Provisional application No. 60/362,899, filed on Mar. 8, 2002.

(51) Int. Cl.
*A61B 5/00* (2006.01)
(52) U.S. Cl. ...................... 600/322; 600/316
(58) Field of Classification Search ............... 600/322, 600/316
See application file for complete search history.

(56) References Cited

U.S. PATENT DOCUMENTS 5,638,816 A * 6/1997 Kiani-Azarbayjany et al. ...... 600/316
6,115,673 A 9/2000 Malin et al.
6,119,026 A * 9/2000 McNulty et al. ............ 600/310
6,157,041 A 12/2000 Thomas et al.
6,280,381 B1 8/2001 Malin et al.
6,415,167 B1 7/2002 Blank
6,441,388 B1 8/2002 Thomas et al.
6,528,809 B1 3/2003 Thomas et al.
2003/0069484 A1 4/2003 Blank et al.

OTHER PUBLICATIONS

S.T. Sum, Spectral Signal Correction for Multivariate Calibration, Doctoral Dissertation, University of Delaware, Summer 1998.

(Continued)

*Primary Examiner*—Eric F. Winakur
*Assistant Examiner*—Matthew J. Kremer
(74) *Attorney, Agent, or Firm*—Michael A. Glenn; Glenn Patent Group

(57) ABSTRACT

A solution for reducing interference in noninvasive spectroscopic measurements of tissue and blood analytes is provided. By applying a basis set representing various tissue components to a collected sample measurement, measurement interferences resulting from the heterogeneity of tissue, sampling site differences, patient-to-patient variation, physiological variation, and instrumental differences are reduced. Consequently, the transformed sample measurements are more suitable for developing calibrations that are robust with respect to sample-to-sample variation, variation through time, and instrument related differences. In the calibration phase, data associated with a particular tissue sample site is corrected using a selected subset of data within the same data set. This method reduces the complexity of the data and reduces the intra-subject, inter-subject, and inter-instrument variations by removing interference specific to the respective data subset. In the measurement phase, the basis set correction is applied using a minimal number of initial samples collected from the sample site(s) where future samples will be collected.

107 Claims, 7 Drawing Sheets

OTHER PUBLICATIONS

D.L. Massart, B.G.M. Vandeginste, S.N. Deming, Y. Michotte and L. Kaufman, Chemometrics: a textbook, New York: Elsevier Science Publishing Company, Inc., 1990.

A.V. Oppenheim and R. W. Schafer, Digital Signal Processing, Englewood Cliffs, NJ: Prentice Hall, 1975, pp. 195-271.

M. Otto, Chemometrics, Weinheim: Wiley-VCH, 1999.

K.R. Beebe., R.J. Pell and M.B. Seasholtz, Chemometrics A Practical Guide, New York: John Wiley & Sons, Inc., 1998.

A. Savitzky and M. J. E. Gotay. Smoothing and Differentiation of Data by Simplified Least Squares Procedures, Anal. Chem., vol. 36, No. 8, pp. 1627-1639, 1964.

H. Martens, T. Naes, Multivariate Calibration, John Wiley and Sons, New York, 1989.

P. Geladi, B. Kowalski, Partial least-squares regression: a tutorial, Analytica Chimica Acta, 185, pp. 1-17, (1986).

S. Haykin, Neural Networks: A Comprehensive Foundation, Prentice Hall, Upper Saddle River NJ (1994).

A. Guyton, J. Hall, Textbook of Medical of Physiology, 9th ed., :Exchange of Nutrients and Other Substances, Philadelphia, W.B. Saunders Company (1996).

M. Van Gernert, S. Jacques, H. Sterenborg, W. Star, Skin optics, IEEE Transactions on Biomedical Engineering, 36: 12, pp. 1146-1154 (Dec, 1989).

B. Wilson, S. Jacques, Optical reflectance and transmittance of tissues: principles and applications, IEEE Journal of Quantum Electronics, 26:12, pp. 2186-2199.

F. Ebling, The Normal Skin, Textbook of Dermatology, 2nd ed.; A. Rock; D. Wilkinson, F. Ebling, Eds.; Blackwell Scientific, Oxford, pp 4-24 (1972).

S. Wilson, V. Spence, A tissue heat transfer model for relating dynamic skin temperature changes to physiological parameters, Phys. Med. Biol., 33:894-897 (1988).

S. Jacques, Origins of tissue optical properties in the UVA, Visible and NIR Regions, Optical Society of America, Topical Meeting, Orlando FL (Mar. 18-22, 1996).

P. Geladi, D. McDougall and H. Martens, Linearization and scatter-correction for near-infrared reflectance spectra of meat, Applied Spectroscopy, vol. 39, pp. 491-500, 1985.

R.J. Barnes, M.S. Dhanoa, and S. Lister, Standard normal variate transformation and de-trending of near-infrared diffuse reflectance spectra, Applied Spectroscopy, 43, pp. 772-777, 1989.

T. Isaksson and B. R. Kowalski, Piece-Wise Multiplicative Scatter Correcton Applied to Near-Infrared Diffuse Transmittance Data from Meat Products, Applied Spectroscopy, vol. 47, pp. 702-709, 1993.

H. Martens and E. Stark, Extended multiplicative signal correction and spectral interference subtraction: new preprocessing methods for near infrared spectroscopy, J. Pharm Biomed Anal, 9, pp. 625-635, 1991.

T. Isaksson, Z. Wang, and B. R. Kowalski, J., Optimised scaling (OS-2) regression applied to near infrared diffuse spectroscopy data from food products, Near Infrared Spectroscopy, 1, pp. 85-97, 1993.

U. Muller, B. Mertes, C. Fischbacker, K. Jagemann, K. Danzer, Noninvasive blood glucose monitoring by means of new infrared spectroscopic methods for improving the reliability of the calibration models, Int J Artif Organs, 20:285-290 (1997).

J. Burmeister, M. Arnold, G. Small, Human noninvasive measurement of glucose using near infrared spectroscopy [abstract], Pittcon, New Orleans LA (1998).

T. Blank, T. Ruchti, S. Malin, S. Monfre, The use of near-infrared diffuse reflectance for the noninvasive prediction of blood glucose, IEEE Lasers and Electro-Optics Society Newsletter, 13:5 (Oct. 1999).

O. Khalil, Spectroscopic and clinical aspects of noninvasive glucose measurements, Clin Chem, 45:165-77 (1999)).

R. Anderson, J. Parrish, The optics of human skin, Journal of Investigative Dermatology, 7:1, pp. 13-19 (1981).

W. Cheong, S. Prahl, A. Welch, A review of the optical properties of biological tissues, IEEE Journal of Quantum Electronics, 26:12, pp. 2166-2185, (Dec. 1990).

D. Benaron, D. Ho, Imaging (NIRI) and quantitation (NIRS) in tissue using time-resolved spectrophotometry: the impact of statically and dynamically variable optical path lengths, SPIE, 1888, pp. 10-21 (1993).

J. Conway, K. Norris, C. Bodwell, A new approach for the estimation of body composition: infrared interactance, The American Journal of Clinical Nutrition, 40, pp. 1123-1140 (Dec. 1984).

S. Homma, T. Fukunaga, A. Kagaya, Influence of adipose tissue thickness in near infrared spectroscopic signals in the measurement of human muscle, Journal of Biomedical Optics, 1:4, pp. 418-424 (Oct. 1996).

A. Profio, Light transport in tissue, Applied Optics, 28:12), pp. 2216-2222, (Jun. 1989).

See Diabetes Statistics, Publication No. 98-3926, National Institutes of Health, Bethesda MD (Nov. 1997).

See The Diabetes Control and Complications Trial Research Group, The effect of intensive treatment of diabetes on the development and . . . N Eng J of Med, 329:977-86 (1993).

M. Robinson, R. Eaton, D. Haaland, G. Keep, E. Thomas, B. Stalled, P. Robinson, Noninvasive glucose monitoring in diabetic patients: A preliminary evaluation, Clin Chem, 38:1618-22 (1992).

H. Heise, R. Marbach, T. Koschinsky, F. Gries, Noninvasive blood glucose sensors based on near-infrared spectroscopy, Artif Org, 18:439-47 (1994).

H. Heise, R. Marbach, Effect of data pretreatment on the noninvasive blood glucose measurement by diffuse reflectance near-IR spectroscopy, SPIE Proc, 2089:114-5 (1994).

R. Marbach, T. Koschinsky, F. Gries, H. Heise, Noninvasive blood glucose assay by near-infrared diffuse reflectance spectroscopy of the human inner lip, Appl Spectrosc, 47: 875-81 (1993).

R. Marbach, H. Heise, Optical diffuse reflectance accessory for measurements of skin tissue by near-infrared spectroscopy, Applied Optics 34(4):610-21 (1995).

K. Jagemann, C. Fischbacker, K. Danzer, U. Muller, B. Mertes, Application of near-infrared spectroscopy for noninvasive determination of blood/tissue glucose using neural network, Z Phys Chem, 191S:179-190 (1995).

C. Fischbacker, K. Jagemann, K. Danzer, U. Muller, L. Papenkrodt, J. Schuler, Enhancing calibration models for noninvasive near-infrared spectroscopic blood glucose determinations, Fresenius J Anal Chem 359;78-82 (1997).

K. Danzer, C. Fischbacker, K. Jagemann, K. Reichelt, Near-infrared diffuse reflection spectroscopy for noninvasive blood-glucose monitoring, LEOS Newsletter 12(2):9-11 (1998).

Ljung, Lennart, Systems Identification: Theory for the User, 2d.ed, Prentice Hall (1999).

Hazen, Kevin H. "Glucose Determination in Biological Matrices Using Near-Infrared Spectroscopy", doctoral dissertation, University of Iowa, 1995.

N. Draper, H. Smith, Applied Regression Analysis, 2d.ed., John Wiley and Sons, New York (1981), principal component regression.

* cited by examiner

MEASUREMENT SITE DEPENDENT DATA PREPROCESSING METHOD FOR ROBUST CALIBRATION AND PREDICTION

CROSS-REFERENCE TO RELATED APPLICATIONS

This application is a continuation-in-part of U.S. patent application Ser. No. 09/630,201 filed on Aug. 1, 2000, now U.S. Pat. No. 6,871,169, which is a continuation-in-part of U.S. patent application Ser. No. 09/610,789 filed Jul. 6, 2000, now abandoned, which is a continuation-in-part of U.S. patent application Ser. No. 08/911,588 filed Aug. 14, 1997, now U.S. Pat. No. 6,115,673; and claims priority to U.S. provisional patent application No. 60/362,899 filed Mar. 8, 2002, each of which is incorporated herein in its entirety by this reference thereto.

BACKGROUND OF THE INVENTION

1. Field of the Invention

This invention relates generally to spectroscopic data processing data technology and its application in calibration and noninvasive measurement of blood analytes, such as glucose. More particularly, this invention relates to a method for attenuating spectroscopic interference resulting from tissue heterogeneity, patient-to-patient variation, instrument related variation, and physiological variation.

2. Background Information

The need for an accurate, noninvasive method for measuring blood analytes, particularly glucose is well understood and documented. Diabetes is a leading cause of death and disability worldwide and afflicts an estimated 16 million Americans. Complications of diabetes include heart and kidney disease, blindness, nerve damage and, high blood pressure with the estimated total cost to United States economy alone exceeding $90 billion per year. *Diabetes Statistics, Publication No.* 98-3926, National Institutes of Health, Bethesda Md. (November 1997). Long-term clinical studies show that the onset of complications can be significantly reduced through proper control of blood glucose levels. *The Diabetes Control and Complications Trial Research Group, The effect of intensive treatment of diabetes on the development and progression of long-term complications in insulin-dependent diabetes mellitus,* N Eng J of Med, 329:977–86 (1993). A vital element of diabetes management is the self-monitoring of blood glucose levels by diabetics in the home environment. A significant disadvantage of current monitoring techniques is that they discourage regular use due to the inconvenience and pain involved in drawing blood through the skin prior to analysis. Therefore, new methods for self-monitoring of blood glucose levels are required to improve the prospects for more rigorous control of blood glucose in diabetic patients.

Numerous approaches have been explored for measuring blood glucose levels, ranging from invasive methods such as microdialysis to noninvasive technologies that rely on spectroscopy. Each method has associated advantages and disadvantages, but only a few have received approval from certifying agencies. To date, no noninvasive techniques for the self-monitoring of blood glucose have been certified.

One method using near-infrared spectroscopy involves the illumination of a spot on the body with near-infrared electromagnetic radiation which is light in the wavelength range 700 to 2500 nm. The light is partially absorbed and scattered, according to its interaction with the tissue constituents prior to being reflected back to a detector. The detected light contains quantitative information that is based on the known interaction of the incident light with components of the body tissue including water, fat, protein, and glucose.

Previously reported methods for the noninvasive measurement of glucose through near-infrared spectroscopy rely on the detection of the magnitude of light attenuation caused by the absorption signature of blood glucose as represented in the targeted tissue volume. The tissue volume is the portion of irradiated tissue from which light is reflected or transmitted to the spectrometer detection system. The spectroscopic signal related to glucose is extracted from the spectral measurement through various methods of signal processing and one or more mathematical models. The models are developed through the process of calibration on the basis of an exemplary set of spectral measurements and associated reference blood glucose values (the calibration set) based on an analysis of capillary (fingertip), alternative invasive, or venous blood.

Near-infrared spectroscopy has been demonstrated in specific studies to represent a feasible and promising approach to the noninvasive prediction of blood glucose levels. One of the studies reports three different instrument configurations for measuring diffuse transmittance through the finger in the 600–1300 nm range. Meal tolerance tests were used to perturb the glucose levels of three subjects and calibration models were constructed specific to each subject on single days and tested through cross-validation. Absolute average prediction errors ranged from 19.8 to 37.8 mg/dL. M. Robinson, R. Eaton, D. Haaland, G. Keep, E. Thomas, B. Stalled, P. Robinson, *Noninvasive glucose monitoring in diabetic patients: A preliminary evaluation,* Clin Chem, 38:1618–22 (1992).

Other studies present results through a diffuse reflectance measurement of the oral mucosa in the 1111–1835 nm range with an optimized diffuse reflectance accessory. In vivo experiments were conducted on single diabetics using glucose tolerance tests and on a population of 133 different subjects. The best standard error of prediction reported was 43 mg/dL and was obtained from a two-day single person oral glucose tolerance test that was evaluated through cross-validation. H. Heise, R. Marbach, T. Koschinsky, F. Gries, *Noninvasive blood glucose sensors based on near-infrared spectroscopy,* Artif Org, 18:439–47 (1994); H. Heise, R. Marbach, *Effect of data pretreatment on the noninvasive blood glucose measurement by diffuse reflectance near-IR spectroscopy,* SPIE Proc, 2089:114–5 (1994); R. Marbach, T. Koschinsky, F. Gries, H. Heise, *Noninvasive glucose assay by near-infrared diffuse reflectance spectroscopy of the human inner lip,* Appl Spectrosc, 47:875–81 (1993) and R. Marbach, H. Heise, *Optical diffuse reflectance accessory for measurements of skin tissue by near-infrared spectroscopy,* Applied Optics 34(4):610–21 (1995).

Some other studies have recorded spectra in diffuse reflectance over the 800–1350 nm range on the middle finger of the right hand with a fiber-optic probe. Each experiment involved a diabetic subject and was conducted over a single day with perturbation of blood glucose levels through carbohydrate loading. Results, using both partial least squares regression and radial basis function neural networks were evaluated on single subjects over single days through cross-validation. An average root mean square prediction error of 36 mg/dL through cross-validation over 31 glucose profiles has also been reported. K. Jagemann, C. Fischbacker, K. Danzer, U. Muller, B. Mertes, *Application of near-infrared spectroscopy for noninvasive determination of blood/tissue glucose using neural network,* Z Phys Chem, 191S:179–190

(1995); C. Fischbacker, K. Jagemann, K. Danzer, U. Muller, L. Papenkrodt, J. Schuler, *Enhancing calibration models for noninvasive near-infrared spectroscopic blood glucose determinations,* Fresenius J Anal Chem 359:78–82 (1997); K. Danzer, C. Fischbacker, K. Jagemann, K. Reichelt, *Near-infrared diffuse reflection spectroscopy for noninvasive blood-glucose monitoring,* LEOS Newsletter 12(2):9–11 (1998); and U. Muller, B. Mertes, C. Fischbacker, K. Jagemann, K. Danzer, *Noninvasive blood glucose monitoring by means of new infrared spectroscopic methods for improving the reliability of the calibration models,* Int J Artif Organs, 20:285–290 (1997).

In a study of five diabetic subjects conducted over a 39-day period with five samples taken per day, absorbance spectra through a transmission measurement of the tongue in the 1429–2000 nm range were collected. Every fifth sample was used for an independent test set and the standard error of prediction for all subjects was greater than 54 mg/dL. J. Burmeister, M. Arnold, G. Small, *Human noninvasive measurement of glucose using near infrared spectroscopy* (abstract), Pittcon, New Orleans La. (1998).

In a study involved in noninvasive measurement of blood glucose during modified oral glucose tolerance tests over a short time period, the calibration was customized for the individual and tested over a relatively short time period. T. Blank, T. Ruchti, S. Malin, S. Monfre, *The use of near-infrared diffuse reflectance for the noninvasive prediction of blood glucose,* IEEE Lasers and Electro-Optics Society Newsletter,13:5 (October 1999).

In all of these studies, limitations are cited that would affect the acceptance of such a method as a commercial product. These limitations include sensitivity, sampling problems, time lag, calibration bias, long-term reproducibility, and instrument noise. Fundamentally, however, accurate noninvasive estimation of blood glucose is presently limited by the available near-infrared technology, the trace concentration of glucose relative to other constituents, and the complex nature of the skin and living tissue of the patient. O. Khalil, *Spectroscopic and clinical aspects of noninvasive glucose measurements,* Clin Chem, 45:165–77 (1999).

As we have discovered, chemical, structural, and physiological variations occur that produce dramatic and nonlinear changes in the optical properties of the tissue sample. S. Malin, T. Ruchti, An Intelligent System for Noninvasive Blood Analyte Prediction, U.S. Pat. No. 6,280,381 (Aug. 28, 2001). Relevant studies may be found in the following references: R. Anderson, J. Parrish, *The optics of human skin,* Journal of Investigative Dermatology, 7:1, pp.13–19 (1981), W. Cheong, S. Prahl, A. Welch, *A review of the optical properties of biological tissues,* IEEE Journal of Quantum Electronics, 26:12, pp.2166–2185, (December 1990), D. Benaron, D. Ho, *Imaging (NIRI) and quantitation (NIRS) in tissue using time-resolved spectrophotometry: the impact of statically and dynamically variable optical path lengths,* SPIE, 1888, pp.10–21 (1993), J. Conway, K. Norris, C. Bodwell, *A new approach for the estimation of body composition: infrared interactance,* The American Journal of Clinical Nutrition, 40, pp.1123–1140 (December 1984), S. Homma, T. Fukunaga, A. Kagaya, *Influence of adipose tissue thickness in near infrared spectroscopic signals in the measurement of human muscle,* Journal of Biomedical Optics, 1:4, pp.418–424 (October 1996), A. Profio, *Light transport in tissue,* Applied Optics, 28:12), pp. 2216–2222, (June 1989), M. Van Gemert, S. Jacques, H. Sterenborg, W. Star, *Skin optics,* IEEE Transactions on Biomedical Engineering, 36:12, pp.1146–1154 (December 1989), and B. Wilson, S. Jacques, *Optical reflectance and transmittance of tissues: principles and applications,* IEEE Journal of Quantum Electronics, 26:12, pp. 2186–2199.

In particular, the characteristics and variation of the tissue sample produce profound interference in the tissue measurement that leads to degradation in the accuracy and precision noninvasive glucose measurements. For example, the near-infrared diffuse reflectance (absorbance) spectrum is a complex combination of the tissue scattering properties that are dominated by the concentration and characteristics of a multiplicity of tissue components including water, fat, protein, and glucose. Physiological variation causes dramatic changes in the tissue measurement over time and lifestyle, health, aging, and environmental exposure lead to spectrally manifested structural variations. Errors in glucose measurements develop when the net analyte signal of glucose is attenuated by interference or when the sample is outside the effective range of the calibration model.

The measurement is further complicated by the heterogeneity of the sample, the multi-layered structure of the skin, changes in the volume fraction of blood in the tissue, hormonal stimulation, temperature fluctuations, and blood analyte levels. This can be further considered through a discussion of the properties of skin.

Tissue Scattering Properties

1. Skin Structure

The structure and composition of skin varies widely among individuals, between different sites within an individual, and over time on the same individual. Skin includes a superficial layer known as the stratum corneum, a stratified cellular epidermis, and an underlying dermis of connective tissue. Below the dermis is the subcutaneous fatty layer or adipose tissue. The epidermis, with a thickness of 10–150 $\mu$m, together with the stratum corneum provides a barrier to infection and loss of moisture and other body constituents, while the dermis is the thick inner layer that provides mechanical strength and elasticity. F. Ebling, *The Normal Skin,* Textbook of Dermatology, $2^{nd}$ ed.; A. Rook; D. Wilkinson, F. Ebling, Eds.; Blackwell Scientific, Oxford, pp 4–24 (1972). In humans, the thickness of the dermis ranges from 0.5 mm over the eyelid to 4 mm on the back and averages approximately 1.2 mm over most of the body. S. Wilson, V. Spence, Phys. Med. Biol., 33:894–897 (1988).

In the dermis, water accounts for approximately 70% of the volume. The next most abundant constituent is collagen, a fibrous protein comprising 70–75% of the dry weight of the dermis. Elastin fibers, also a protein, are plentiful though they constitute a smaller proportion of the bulk. In addition, the dermis contains a wide variety of structures (e.g., sweat glands, hair follicles, and blood vessels) and other cellular constituents. F. Ebling, supra. Conversely, the subcutaneous layer (adipose tissue) is by volume approximately 10% water and is composed primarily of cells rich in triglycerides or fat. The concentration of glucose varies in each layer according to a variety of factors which include the water content, the relative sizes of the fluid compartments, the distribution of capillaries, the perfusion of blood, the glucose uptake of cells, the concentration of glucose in blood, and the driving forces (e.g. osmotic pressure) behind diffusion. Due to the high concentration of fat, the average concentration of water soluble glucose in subcutaneous tissue is significantly lower than that of the dermis.

2. Skin Properties

Noninvasive technologies measure the alteration of a probing or excitation signal, such as near-infrared radiation, emitted radiation from the body, and radio wave, by specific properties of tissue, such as absorption, scattering, impedance, optical rotation, and fluorescence. However, other sample constituents of tissue often interfere, and the specific response, (the alternation of the probing or excitation signal due to or related to glucose) is greatly attenuated or completely obscured.

For example, one may consider the measurement of glucose through near-infrared spectroscopy on the basis of the absorption of glucose. In a near-infrared absorption spectrum, a change in the concentration of glucose is reflected by a change in the absorption of light according to the absorption and scattering properties of glucose and/or the effect of glucose changes upon the anatomy and physiology of the sampled site. However, in addition to the effect of glucose on the near-infrared light probing signal that is delivered to the skin, the probing signal is also reflected, diffusely reflected, transmitted, scattered, and absorbed in a complex manner related to the structure and composition of the tissue. When near-infrared light is delivered to the skin, a percentage of it is reflected, while the remainder penetrates into the skin. The proportion of reflected light, or specular reflectance, is typically between 4–7% of the delivered light over the entire spectrum from 250–3000 nm for a perpendicular angle of incidence. J. Parrish, R. Anderson, F. Urbach, D. Pitts, UV-A: *Biologic Effects of Ultraviolet Radiation with Emphasis on Human Responses to Longwave Ultraviolet*, New York, Plenum Press (1978). The 93–96% of the incident light that enters the skin is attenuated due to absorption and scattering within many layers of the skin. These two processes, combined with the orientation of the spectrometer sensors, determine the tissue volume irradiated by the source and "sampled" through the collection of diffusely reflected light.

Diffuse reflectance or remittance is defined as that fraction of incident optical radiation that is returned from a turbid sample as a function of wavelength. Alternately, diffuse transmittance is the fraction of incident optical radiation that is transmitted through a turbid sample. Absorption by the various skin constituents mentioned above accounts for the spectral extinction of the light within each layer. Scattering is the main process by which the beam may be returned to contribute to the diffuse reflectance of the skin. Scattering also has a strong influence on the light that is diffusely transmitted through a portion of the skin.

The scattering of light in tissues is in part due to discontinuities in the refractive indices on the microscopic level, such as the aqueous-lipid membrane interfaces between each tissue compartment or the collagen fibrils within the extracellular matrix. B. Wilson, S. Jacques, *Optical reflectance and transmittance of tissues: principles and applications,* IEEE Journal of Quantum Electronics, 26:12 (December 1990). The spatial distribution and intensity of scattered light depends upon the size and shape of the particles relative to the wavelength, and upon the difference in refractive index between the medium and the constituent particles. The scattering of the dermis is dominated by the scattering from collagen fiber bundles in the 2.8 $\mu$m diameter range occupying twenty-one percent of the dermal volume, and the refractive index mismatch is 1.38/1.35 S. Jacques, *Origins of tissue optical properties in the UVA, Visible and NIR Regions, Optical Society of America,* Topical Meeting, Orlando Fla. (Mar. 18–22, 1996). The spectral characteristics of diffuse remittance from tissue result from a complex interplay of the intrinsic absorption and scattering properties of the tissue, the distribution of the heterogeneous scattering components, and the geometry of the point(s) of irradiation relative to the point(s) of light detection.

The near-infrared absorption of light in tissue is primarily due to overtone and combination absorbances of C—H, N—H, and O—H functional groups. As skin is primarily composed of water, protein, and fat; these functional groups dominate the near-IR absorption in tissue. As the main constituent, water dominates the near-infrared absorbance above 1100 nm and is observed through pronounced absorbance bands at 1450, 1900, and 2600 nm. Protein in its various forms, in particular, collagen is a strong absorber of light that irradiates the dermis. Near-infrared light that penetrates to subcutaneous tissue is absorbed primarily by fat. In the absence of scattering, the absorbance of near-infrared light due to a particular analyte, A, can be approximated by Beer's Law at each wavelength by:

$$A = \epsilon c l \qquad (1)$$

where a is the analyte specific absorption coefficient, c is the concentration and l is the pathlength. An approximation of the overall absorbance at a particular wavelength is the sum of the individual absorbance of each particular analyte given by Beer's Law. The concentration of a particular analyte, such as glucose, can be determined through a multivariate analysis of the absorbance over a multiplicity of wavelengths because a is unique for each analyte. However, in tissue compartments expected to contain glucose, the concentration of glucose is at least three orders of magnitude less than that of water. Given the known extinction coefficients of water and glucose, the signal targeted for detection by reported approaches to near-infrared measurement of glucose, i.e. the absorbance due to glucose in the tissue, is expected to be, at most, three orders of magnitude less than other interfering tissue constituents. Therefore, the near-infrared measurement of glucose requires a high level of sensitivity over a broad wavelength range. Multivariate analysis is often utilized to enhance sensitivity.

In addition, the diverse scattering characteristics of the skin, e.g. multiple layers and heterogeneity, cause the light returning from an irradiated sample to vary in a highly nonlinear manner with respect to tissue analytes, in particular, glucose. Simple linear models, such as Beer's Law have been reported to be invalid for the dermis. R. Anderson, J. Parrish, *The optics of human skin,* Journal of Investigative Dermatology, 77:1, pp. 13–19 (1981). Such nonlinear variation is a recognized problem and several reports have disclosed unique methods for compensating for the nonlinearity of the measurement while providing the necessary sensitivity. S. Malin, et al., supra; E. Thomas, R. Rowe, *Methods and apparatus for tailoring spectroscopic calibration Models,* U.S. Pat. No. 6,157,041 (Dec. 5, 2000).

Dynamic Properties of the Skin

While knowledge and utilization of skin properties, high instrument sensitivity, and compensation for inherent non-linearities are all vital to the application of noninvasive technologies in blood analyte measurement, an understanding of the biological and chemical mechanisms that lead to time dependent changes in the properties of skin tissue is equally important and yet, largely ignored. At a given measurement site, skin tissue is often assumed to remain static, except for changes in the target analyte and other interfering species. However, variations in the physiological state and fluid distribution of tissue profoundly affect the optical properties of tissue layers and compartments over a relatively short period of time. Such variations are often dominated by fluid compartment equalization through water shifts and are related to hydration levels and changes in blood analyte levels. A. Guyton, J. Hall, *Textbook of Medical of Physiology*, 9th ed., Philadelphia, W.B. Saunders Co. (1996).

Problem Statement and Description of Related Technology

A major difficulty in the noninvasive measurement of biological constituents and analytes in tissue through near-infrared spectroscopy arises from the fact that many constituents, such as glucose, are present in very small concentrations compared to sources of interference. In particular, the complex, heterogeneous and dynamic composition of the skin, together with profound variation over time, between tissue sample sites within a patient and from patient-to-patient interferes with and thereby attenuates the net analyte signal of many target analytes, such as glucose. In addition, the actual tissue volume sampled and the effective or average pathlength of light are varied. Therefore, the optical properties of the tissue sample are modified in a highly nonlinear and profound manner that introduces significant interference into noninvasive tissue measurements. Both calibration and measurement using noninvasive measurement devices would benefit from a method that attenuates the components of spectral interference related to the heterogeneity of the tissue, patient-to-patient differences, and variation through time (e.g., physiological effects).

Several methods are reported to compensate in some part for the dynamic variation of the tissue and patient-to-patient differences. For example, noninvasive measurement of glucose through calibration models that are specific to an individual over a short period of time are reported. K. H. Hazen, *Glucose determination in biological matrices using near-infrared spectroscopy*, Doctoral Dissertation, University of Iowa (August 1995); J. J. Burmeister, *In vitro model for human noninvasive blood glucose measurements,*" Doctoral Dissertation, University of Iowa (December 1997).

This approach avoids modeling the differences between patients and therefore cannot be generalized to more individuals. In addition, the calibration models have not been tested over long time periods and do not provide a means for correcting for variation related to sample sites or physiological effects.

Several other approaches exist that employ diverse pre-processing methods to remove spectral variation related to the sample and instrumental variation including multiplicative signal correction (P. Geladi, D. McDougall and H. Martens, *Applied Spectroscopy*, vol. 39, pp. 491–500, 1985), standard normal variate transformation (R. J. Barnes, M. S. Dhanoa, and S. Lister, *Applied Spectroscopy*, 43, pp. 772–777, 1989), piecewise multiplicative scatter correction (T. Isaksson and B. R. Kowalski, *Applied Spectroscopy*, 47, pp. 702–709, 1993), extended multiplicative signal correction (H. Martens and E. Stark, *J. Pharm Biomed Anal*, 9, pp. 625–635, 1991), pathlength correction with chemical modeling and optimized scaling (T. Isaksson, Z. Wang, and B. R. Kowalski, *J. Near Infrared Spectroscopy*, 1, pp. 85–97, 1993), and FIR filtering (S. T. Sum, *Spectral Signal Correction for Multivariate Calibration*, Doctoral Dissertation, University of Delaware, 1998). In addition, a diversity of signal, data, or pre-processing techniques are commonly reported with the fundamental goal of enhancing accessibility of the net analyte signal. D. L. Massart, B. G. M. Vandeginste, S. N. Deming, Y. Michotte and L. Kaufman, *Chemometrics: a textbook*, Elsevier Science Publishing Company, Inc., pp. 215–252,1990; A. V. Oppenheim and R. W. Schafer, *Digital Signal Processing*, Englewood Cliffs, Prentice Hall, 1975, pp. 195–271; M. Otto, *Chemometrics*, Weinheim: Wiley-VCH, 1999; and K. R. Beebe., R. J. Pell and M. B. Seasholtz, *Chemometrics A Practical Guide*, John Wiley & Sons, Inc., pp. 26–55, 1998. Notably, Sum describes a solution to variation due to changes in a given physical sample and instrumental effects through the use of signal preprocessing techniques. The reported method reduces the variance in the spectral measurement arising from non-chemical sources while retaining the variance caused by chemical change. The sources of variance include the physical traits of the sample(s), such as, particle size and shape, packing density, heterogeneity, and surface roughness. The method includes preprocessing through a derivative step (see A. Savitzky and M. J. E. Golay. *Smoothing and Differentiation of Data by Simplified Least Squares Procedures*, Anal. Chem., vol. 36, no. 8, pp. 1627–1639, 1964) followed by a spectral transformation through either multiplicative scatter correction or standard normal variate transformation. In addition, a FIR filter is described which for certain applications is found to be more effective in reducing both the instrumental and sample related variation.

While methods for preprocessing effectively compensate for variation related to instrument and physical changes in the sample and enhance the net analyte signal in the presence of noise and interference, they are inadequate for compensating for the sources of tissue related variation defined above. For example, the highly nonlinear effects related to sampling different tissue locations cannot be effectively compensated for through a pathlength correction because the sample is multi-layered, heterogeneous, and leads to large nonlinear variation. In addition, fundamental assumptions inherent in these methods, such as the constancy of multiplicative and additive effects across the spectral range and homoscadasticity of noise are violated in the noninvasive tissue application.

E. V. Thomas and R. K. Rowe have disclosed a method for reducing intra-subject variation through the process of mean-centering both the direct and indirect measurements for calibration and prediction. E. V. Thomas and R. K. Rowe, Methods and Apparatus for Tailoring Spectroscopic Calibration Models, U.S. Pat. No. 6,157,041 (Dec. 5, 2000). However, that patent does not address the key problem related to sample heterogeneity and complexity, physiological and chemical variation related to the dynamic nature of the tissue, and the common problem of optical variation that occurs from sample-to-sample. In addition, the method is applied to the raw spectroscopic measurement and, as a result, it is dominated by variation resulting from surface effects such as surface roughness, hydration, coupling efficiency, and reflectance.

In view of the problems left unsolved by the prior art, there exists a need for a method and apparatus to reduce interference in tissue measurements related sample heterogeneity, time related variations, patient-to-patient differences, and instrumental effects.

SUMMARY OF THE INVENTION

This invention is an improvement of the invention described in U.S. Pat. No. 6,115,673 (herein after '673 patent), entitled *Method and Apparatus for Generating Basis Sets for Use in Spectroscopic Analysis*, issued to S. Malin and K. Hazen on Sep. 5, 2000. In the '673 patent, we disclosed a method for enhancing a net analyte signal related to a particular analyte by transforming the corresponding spectroscopic measurement pursuant to a basis set. The basis set includes a spectral representation of at least one component found in a sample that is typically a source of interference. The spectral measurement is transformed by the removal of the signal related to the basis set from the spectral measurement.

In this invention, we have modified the approach disclosed in '673 patent and extended it to various sources of interference related to the bulk properties of the tissue. Specifically, we have identified the following components as sources of interference: (1) tissue heterogeneity (i.e. sampling location); (2) structural and compositional differences patient-to-patient; (3) time dependent sources of interference (e.g. physiological variation); and (4) instrument variation (i.e. instrument-to-instrument differences and instrument variation through time)

The solution according to this invention includes reduction of the identified sources of interference through the measurement of a "tissue" basis set and the subsequent transformation of a spectroscopic measurement. The transformed measurement is used to estimate the concentration of an analyte through the application of a multivariate calibration model.

The tissue basis set is generated for each patient, sample-site, time period, and instrument and represents the interfering background signal related to the overall optical properties of the tissue. When an apparatus is used to constrain the interference related to tissue heterogeneity, the basis set contains only interference specific to a patient, a physiological state or time period, and an instrument.

Due to the time dependent properties of the sampled tissue, the basis set is collected within a close proximity in time to the spectral measurement. In addition, the transformation of the spectral measurement via the basis set introduces an offset to the analyte measurement that is corrected through a bias adjustment.

The invention leads to the attenuation of tissue variability that is manifested in spectral measurements. During the process of calibration, the reduction in spectral interference leads to parsimonious and robust models that can be applied to a broader range of different tissue types, characteristics, and conditions.

The solution according to this invention has numerous advantages. For examples: First, it is particularly effective for attenuating the common and significant source of sample-to-sample spectral interference related to tissue heterogeneity and errors in the tissue volume that is sampled;

Second, a method is given that leads to the attenuation of spectral interference related to the dynamic properties of the tissue;

Third, the method of attenuation is uniquely determined for each tissue location and physiological state through the generation of a basis set, and thus the attenuation of the interference is significantly improved over methods that utilize common preprocessing steps for these diverse situations;

Fourth, the method of interference attenuation is optimized with respect to patient, instrument, tissue sampling site, and physiological state/condition (all major sources of interference that limit the performance of noninvasive measurement systems);

Further, the method is applied subsequent to standard preprocessing of the spectra and as a result is not dominated by variation related to surface effects; and Finally, the method provides a unique and sensitive method of determining when the tissue location or state is not suitable for measurement of glucose noninvasively.

DETAILED DESCRIPTION OF THE INVENTION

The following discussion describes a solution for improving the accuracy of noninvasive analyte determination through the reduction of major sources of interference. The solution uses a representation of the interference in the form of a tissue basis set to transform tissue measurements such that the signal related to the target analyte is enhanced and more accessible. The transformed measurement is then used as part of a larger set to develop a multivariate calibration model or to estimate the concentration of an analyte in tissue through the application of a previously developed multivariable calibration model.

The solution comprises the following steps: (1) development of a basis set that includes at least one interfering component, (2) adjustment of noninvasive tissue measurements using the basis set, (3) multivariable analysis for calibration development, and (4) noninvasive analyte measurement. In addition, it is beneficial to both the calibration process and noninvasive analyte measurement to perform a bias adjustment to the reference analyte values and the analyte measurements, respectively. Further, the solution also includes steps of outlier detection and preprocessing.

Exemplary Noninvasive Sensor 100

Figure 1:
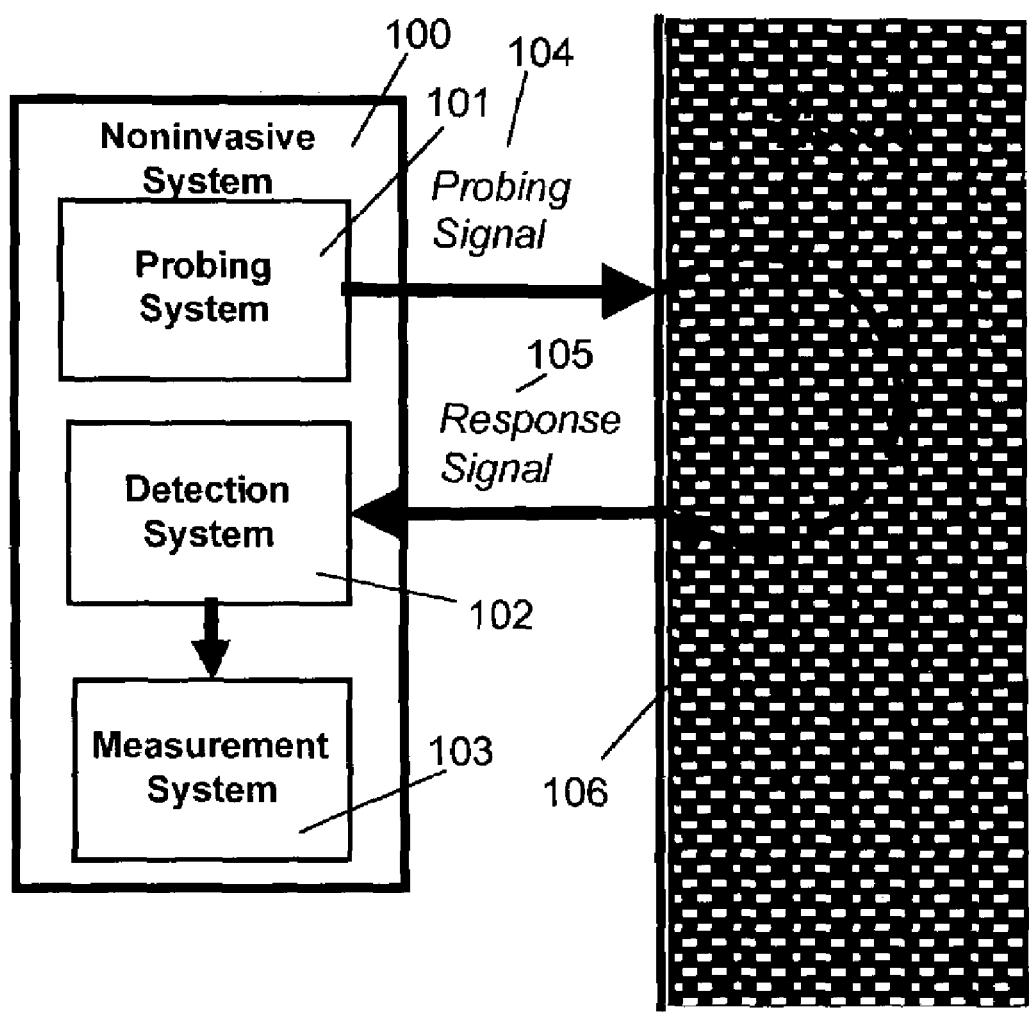
FIG. 1 is schematic block diagram illustrating a noninvasive sensor comprising a probing system, a detection system, and a measurement system.

FIG. 1 is schematic block diagram showing an exemplary noninvasive sensor 100, which comprises a probing system 101, a detection system 102 and a measurement system 103. The probing system 101 utilizes an excitation or probing signal 104 to sample or probe a volume of tissue 106 in the body. A suitable location on the body for measurement may be found on the fingers, palmar region, hand, forearm, upper arm, eye, leg, plantar region, feet, toes, abdomen, earlobe, or torso although other positions are possible. The probing signal is unique to specific technologies and can be, for example, near-infrared light, electromagnetic radiation, visible light, heat, an electrical current, a radio wave, or ultrasound. While FIG. 1 depicts the probing signal 104 originating in the sensor 100, in an alternate embodiment, the probing signal 104 can originate either from a different source not connected to the sensor 100 or from within the body itself. The probing signal 104 interacts with the tissue and the sensor detects a portion of the modified probing signal (i.e. response signal) 105. The tissue volume 106 that is "sampled" is the portion of probed tissue from which the modified probing signal 105 is detected by the sensor 100.

The detection system 102 detects a portion of the modified probing signal 105 and ultimately converts the detected signal, referred to as the "tissue measurement", $m \in \Re^{1 \times N}$ where N corresponds to the dimensionality of the measurement, into a digitized form for analysis in the measurement system 103. For example, in the case of near-infrared spectroscopy, the tissue measurement, commonly denoted by I, refers to the intensity spectrum of the tissue sample represented by the intensity at N wavelengths (or wavelength ranges or selected wavelengths) selected from the 700–2500 nm wavelength range.

In the preferred embodiment of the invention, a background or reference, $I_0$, may be used to standardize or normalize the tissue measurement $m \in \Re^{1 \times N}$. Typically, the reference is collected either simultaneously with the in-vivo measurement, I, or within a close time interval. The reference is a representation of the probing signal 104 applied to the tissue and is used to determine the nature and extent of the modification of the probing signal that occurs due to the interaction of the probing signal 104 and the sampled tissue volume 106. In addition, $I_0$ is used to standardize I against instrument related variation. Typically, I and $I_0$ are either ratio-ed or subtracted. For example, in the case of near-infrared spectroscopy, the absorbance of light by the sampled tissue volume is estimated according to the calculation:

$$A = -\log_{10}\left(\frac{I}{I_0}\right) \qquad (2)$$

where $I_0$ is an estimate of light incident on the sample, I is an intensity spectrum of light detected and A represents an absorbance spectrum containing quantitative information that is based on the known interaction of the incident light with components of the body tissue.

Figure 2:
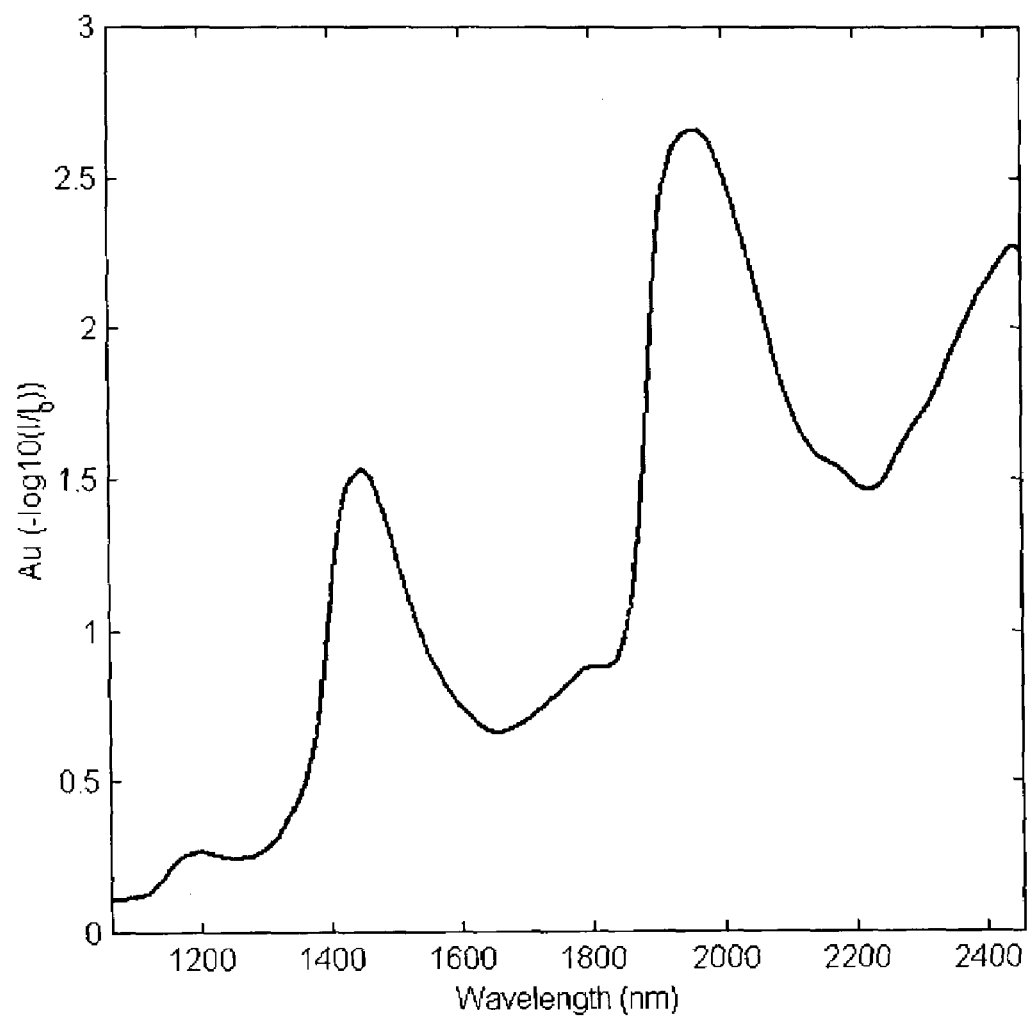
FIG. 2 is a plot of typical absorbance spectrum measurement from the forearm of a human subject.

FIG. 2 is a plot of A versus wavelength, showing a typical absorbance spectrum measurement from the forearm of a human subject. The absorption bands occur primarily due to water, fat, and protein. More particularly, however, the tissue measurement may include a specific set of wavelengths in the near-infrared region that have been optimized for the extraction of features and for the measurement requirements. For example, the noninvasive measurement of glucose has been found to optimally perform in the wavelength range 1100 to 1935 nm, or a selected subset thereof such as 1150 to 1850 nm.

Alternatively, I can be referenced to a representation of the tissue measurement at some point in time prior to the collection of I and can be determined from a single tissue measurement or from the mean or a robust estimate of the mean (e.g., the trimmed mean) of several tissue measurements. Finally, I may include either a single tissue measurement collected with an instrument or a combination of several optimally selected tissue measurements collected over a defined measurement period and averaged. Methods for selecting the tissue measurement, used to produce the lowest noise measurement, include similarity or distance measures (i.e., select the most similar), or clustering operations.

As indicated above, a tissue measurement, I is passed from the detection system 102 to a measurement system 103. The measurement system 103 constitutes a processing device embodying the measurement process depicted in FIG. 3. Note that the processing device of this invention may constitute a computer system or similar electronic computing device that manipulates and transforms data represented as physical/electrical quantities within the computer system's registers and memories into other data similarly represented as physical quantities within the computer system memories or registers, or other such information storage, transmission or display devices. Furthermore, the processing device may constitute a microprocessor, microcontroller, or other processing device incorporated into an apparatus specifically constructed for the purposes of the invention. Alternately, the invention may include one or more logic devices specifically configured or programmed to perform the steps of the invented method. The process shown in FIG. 3 is embodied as computer-readable code stored in a computer readable storage medium such as, but not limited to: any type of disk medium, both fixed and removable, read-only memories (ROM's) including EPROM and EEPROM, random access memories (RAM's), magnetic or optical cards, or any type of medium suitable for storing electronic instructions and data.

The designation of the tissue measurement by the variable "m" is used to refer to the signal that is supplied by the system for analysis and may be, for example, either I or A as described previously.

Measurement System 103

Figure 3:
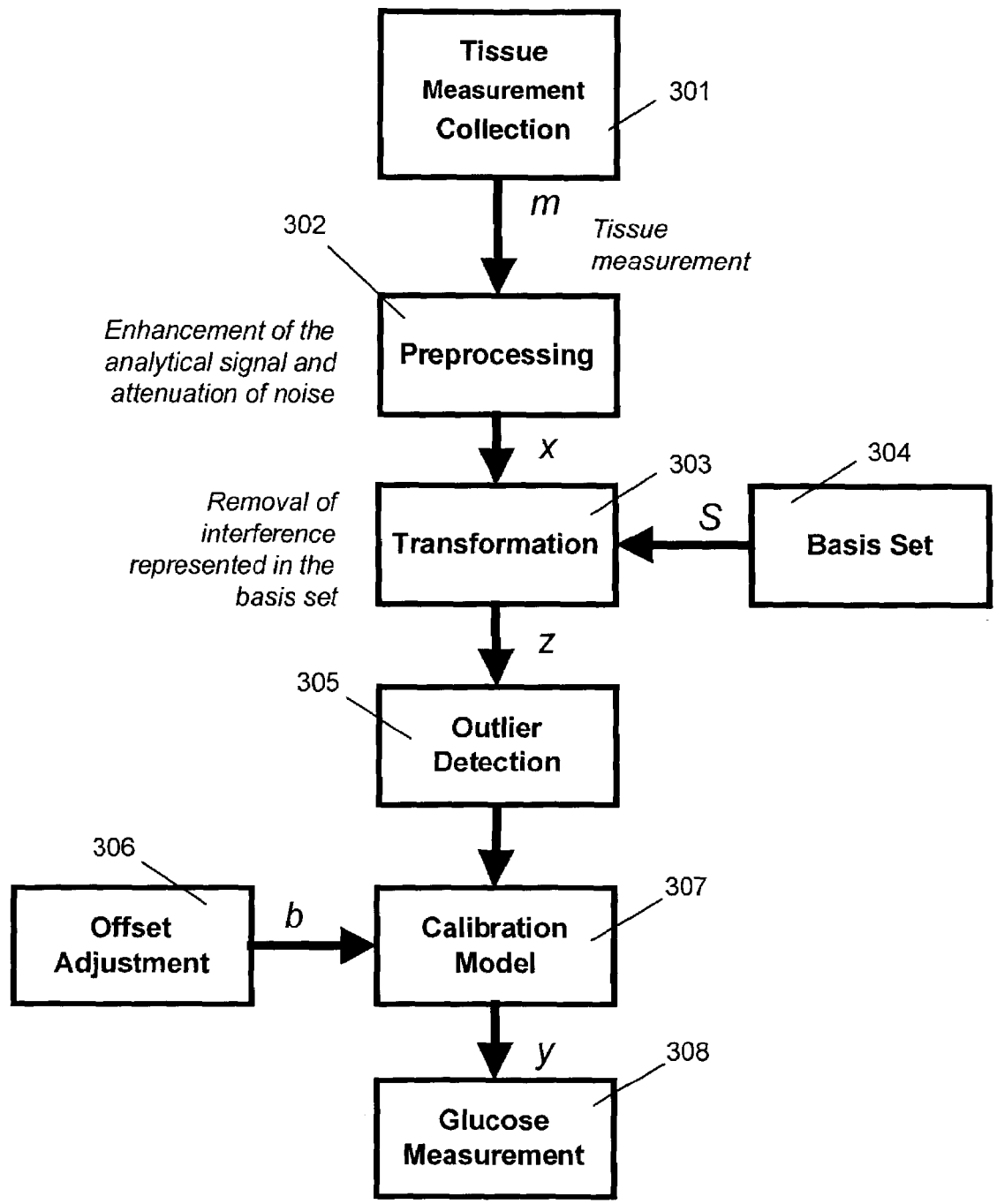
FIG. 3 is a flow diagram illustrating the operation steps of the noninvasive measurement system according to this invention.

The noninvasive measurement of blood chemistry such as a blood analyte, as shown in FIG. 3, involves collecting a tissue measurement 301 described in the prior section, preprocessing the tissue measurement for enhancing the analytical signal and attenuating noises 302, applying a basis set to the preprocessed tissue measurement 304 to transform the preprocessed tissue measurement 303, performing an outlier detection 305, making a bias correction term 306, applying a multivariate calibration model to the transformed tissue measurement 307, and determining such as displaying the measurement of the analyte digitally or/and graphically 308.

The processing may be performed in a field programmable gate array (FPGA) and in a laptop CPU. Other typical devices that may be employed include a complex programmable logic device (CPLD), an embedded processor, a microprocessor, or a specialized signal processing chip. Typically, the FPGA or CPLD is utilized early in the digital train, but may be employed at later stages.

Basis Set Measurement 304

A tissue basis set, denoted by $S \in \Re^{P \times N}$, is a set of P vectors that represents components of interference present in a tissue sample. The basis set is formed through the collection of tissue measurements, $m \in \Re^{1 \times N}$, at various times and tissue locations under diverse conditions. For example, the basis set is generated with the first n measurements of a day, wherein $n \geq 1$. For another example, the basis set may be generated with the last n measurements prior to a current sample, wherein $n \geq 1$. Further, the basis set may be generated with a moving series of samples as in a time series analysis. For example, for current spectrum n, the n–10 to n–2 samples may be utilized to generate the basis set if the reference values are availiable.

The principal sources of interferences identified include:
1. Tissue heterogeneity (sampling location);
2. Patient-to-patient structural and compositional differences;
3. Time dependent sources of interference (e.g., physiological variation); and
4. Instrumental variation (instrument-to-instrument differences and instrument variation through time).

It is important to note that a different tissue basis set is generated for each patient, sample-site, instrument, and time period and represents the interfering background signal related to the overall optical properties of the tissue. When an apparatus is used to constrain the interference related to tissue heterogeneity, the basis set contains only interference specific to a patient, a physiological state or time period, and an instrument.

More specifically, the basis set is a set of tissue measurements that are processed and combined according to noise requirements and the type of variation represented. Therefore, the basis set is a set of tissue measurements that are collected at various tissue sample sites on a particular patient and associated with a particular time period and instrument. The tissue measurements are used for a finite time period subsequent to their collection and are associated with a particular patient, physiological state, and instrument. When an apparatus is employed to ensure the sample site is repeatable, the basis set is reduced and typically contains only one measurement, termed the "tissue template." In this latter embodiment, multiple tissue measurements may be averaged to form the tissue template.

When the noninvasive sensor is applied to measure an analyte, as depicted in FIG. 3, the basis set is normally collected and calculated prior to the collection of additional tissue measurements. In applications involving post-processing, or the collection of multiple tissue measurements prior to producing an analyte measurement, the basis set may be calculated from a multiplicity of tissue measurements spanning the time period of applicability. This time period is generally less than 24 hours. It is beneficial to preprocess the basis set to attenuate random noise, baseline variation associated with the instrument, variation related to surface contact, and low frequency interference related to scattering. Preprocessing steps include filtering, averaging, derivative calculations, multiplicative scatter correction, smoothing, and normalization. As indicated by FIG. 3, the basis set 304 is applied to transform 303 preprocessed tissue measurements, x, to produce the corrected measurement, z. Therefore, it is necessary that the methods and steps used to preprocess the basis set be identical to those applied in the preprocessing step 303 of FIG. 3 to tissue measurements.

For example, we consider an application in which the guide system is used to constrain the sample-to-sample variability of a near-infrared diffuse reflectance tissue measurement by the attachment of a guide to the sample measurement site. At the time of guide attachment, a tissue measurement is, collected after inserting an optical probe into the guide aperture. Several tissue measurements associated with various probe placements within the aperture are subsequently taken. The set of tissue measurements or near-infrared spectra, each associated with a different probe insertion. One or more of these spectra may be utilized in the formation of a basis set. For example, the spectra may be processed through the following steps: filtering via a 15-point Savitsky-Golay first derivative and wavelength selection (1150–1950 nm). The resulting set of preprocessed tissue measurements forms the basis set associated with the guide attachment to the arm and is used to transform all subsequent preprocessed tissue measurements collected using the same guide attachment. Alternately, the preprocessed set of tissue measurements are averaged using either a mean calculation or a robust estimate of the mean (e.g., trimmed mean) and the resulting averaged processed tissue measurement is the basis set or the tissue template.

In a second example, a guide system is not employed and six tissue measurements are collected in a localized area of the tissue, each associated with a different sampling location. The set of tissue measurements are processed through the following steps: filtering through a 15-point Savitsky-Golay first derivative and wavelength selection. The resulting set of six preprocessed tissue measurements forms the basis set associated with the current sampling conditions such as those related to patient, instrument, and time period.

While the application of the basis set to calibration and measurement data is the same, the selection of the basis set is different. In the case of the calibration set, the basis set may be comprised of a subset of the calibration data or a set of processed tissue measurements that is derived from the calibration set. When a calibration set is collected, several basis sets are selected from the individual calibration samples and combined to form a robust estimate of the mean over a short time interval, for a particular subject, instrument, and probe placement. If more than one sampling location is used per subject, a cluster analysis may be performed to determine a basis set capable of representing a continuum of probe placements. For example, a set of calibration data was collected on 17 subjects and two instruments. Each subject participated in one to three different visits (days of experimentation) and on each visit a guide system was employed to constrain the tissue sampling location. A separate basis set was determined for each subject, visit, and instrument by (1) first preprocessing each tissue measurement and (2) calculating the mean of all preprocessed tissue measurements associated with each subject, visit, and instrument.

Finally, in certain applications it is desirable to optimize the selection of tissue measurements used to create a basis set. The purpose for selecting an optimal subset of samples is to capture the characteristic background that is comprised of the primary energy absorbing and scattering constituents in the tissue. The inclusion of samples with slight spectral variations not related to these tissue constituents results in the computation of an unrepresentative basis set and leads to a less efficient correction of the data. Four methods are disclosed for performing sample selection prior to the determination of a basis set.

The first method is to compute a robust estimate of the mean (preprocessed) of the data set targeted for the basis set. Specifically, the trimmed mean is calculated by excluding the highest and lowest 25% of values at each wavelength or variable prior to averaging.

The second method is to perform a Principal Component Analysis (PCA) and to remove samples that contain high leverage with respect to the sample population. Several methods are employed using PCA such as a leave-one-out analysis of the captured covariance from the resulting PCA eigenvalues. Samples which when left out result in a drop in covariance greater than a preset limit are removed. In an alternate embodiment a T-Squared or Q-Test of the Principal Component scores is performed. Samples exceeding a defined confidence interval are excluded from the basis set computation.

The third method for selecting a subset of samples is to process known spectral features into quantifiable information that is used to determine the state of the tissue encountered. Spectral bands that contain information related to fat, water, protein, surface reflectance, probe-to-surface contact, etc. is compressed into single property values through processing and then used individually or in combinations, either linear or by complex functionality, to determine samples that have information most consistent with the current optical state of the tissue. Samples associated with inconsistent optical states with respect to the calibration set or property values exceeding those predefined through calibration are excluded. The remaining samples are to compute the basis set.

The final method involves propagating the collected spectral measurements through a rudimentary predictive model and comparing the resulting analyte estimates to spectral features that are related to key optical characteristics of the encountered tissue. Measurements that have a high correlation to extracted features related to sampling anomalies, such as surface reflectance, are excluded from the sample population. The remaining samples are used to compute the basis set.

The basis set is typically generated prior to data collection. For the case of subtracting off the initial spectrum of the day, the basis set is the first spectrum or a processed version of it. However, in some instances all of the data is required prior to generation of the basis set. For example, if we were to subtract out the mean spectrum of the day, then we would need all of the spectra prior to processing. For a time-series based basis set, we would utilize data up until the point of data collection in the formation of the basis set.

Transformation 303 by Applying Basis Set 304

Referring to FIG. 3, the noninvasive system 301 collects a tissue measurement, m, that is subjected to preprocessing 302 corresponding to the preprocessing performed on the basis set tissue measurements. Subsequently, the preprocessed tissue measurement, x, is transformed 303 for the purpose of attenuating interference as described previously. The tissue measurement is applied to the basis set through a transformation and a set of normalization parameters according to $$z = f(x, S, P) \quad (3)$$

where z is the transformed spectral measurement, S is the basis set and P is the set of weights or normalization parameters. The transformation, $f(?)$, is a function that is used to attenuate the interference represented by S that is contained in x. The methods used for transformation may include: subtraction or a weighted subtraction, division, deconvolution, multiplicative scatter correction, and rotation.

In the preferred embodiment, the transformation occurs through $$z = x - (c^T S + d) \quad (4)$$

where $c \in \Re^{1 \times P}$ is used to weight each member of the tissue basis set to optimally reduce the interference in x and $d \in \Re^{1 \times N}$ is an intercept adjustment. The coefficients c and d are either preset or determined through multiple linear regression. An extension of this embodiment occurs when one tissue sample site is used. In this case, the basis set consists of one processed tissue measurement associated with a particular time and guide placement and the basis set is applied to the processed tissue measurement through $$z = x - S. \quad (5)$$

Noninvasive Analyte Measurement Through Calibration 307

The measurement of an analyte, as shown in FIG. 3, is accomplished through the application of a calibration model 307 to the processed tissue measurement, x, after correction via the tissue basis set, S and outlier detection 305. Therefore, prior to the analyte measurement a calibration model or equation is determined. The calibration model is given by $$\hat{y} = f(z) + b; \quad (6)$$

where $\hat{y}$ is the estimated glucose concentration, $z \in \Re^{1 \times N}$ is a processed and transformed tissue measurement, $f: \Re^N \to \Re^1$ is a model used to measure glucose on the basis of the preprocessed and transformed tissue measurement, and b is an offset adjustment 306 for the glucose measurement.

The calibration model is determined from a calibration set of exemplary paired data points each including a preprocessed and transformed (via tissue basis set) tissue measurement and an associated reference analyte value (y) determined from an analysis of a blood or interstitial fluid sample. As described previously, in calibration development, a basis set is developed for each patient and time period in order to account for the short-term optical tissue property changes observed in an individual over time and to correct for gross optical tissue property differences between individuals. The resulting set of preprocessed and transformed tissue measurements and corresponding reference analyte values is used to calculate the calibration model, $f(.)$. Designing the structure of $f(.)$ is through the process of system of identification as introduced by L. Ljung, *Systems Identification: Theory for the User*, 2d.ed, Prentice Hall (1999). The model parameters are calculated using known methods including multivariate regression or weighted multivariate regression (N. Draper and H. Smith, *Applied Regression Analysis*, 2d.ed., John Wiley & Sons, New York, 1981), principal component regression (H. Martens, T. Naes, *Multivariate Calibration*, John Wiley & Sons, New York, 1989), partial least squares regression (P. Geladi, B. Kowalski, *Partial least-squares regression: a tutorial*, Analytica Chimica Acta, 185, pp.1–17, 1986), or artificial neural networks (S. Haykin, *Neural Networks: A Comprehensive Foundation*, Prentice Hall, Upper Saddle River N.J., 1994).

In the preferred embodiment the calibration model is linear:

$$\hat{y} = zF + b; \quad (7)$$

where $F \in \Re^{N \times 1}$ and b is an offset adjustment 306 for the glucose measurement. The determination of F is through partial least squares regression with 15 factors. Alternately, an artificial neural network is employed. For example, after re-sampling z every 10 nm, a neural network may utilize one hidden layer with eight nodes. Additionally, it is important to note that more than one model may be used for a given application as previously disclosed.

After the development of a calibration and the collection of a basis set specific to a patient, time period, and instrument, measurements occur according to the process shown in FIG. 3.

Optionally, the bias corrected tissue measurements, z, undergo an outlier detection step 305. The spectra that we collect in a noninvasive glucose measurement are complex as is the data processing that follows. There are many situations in which the physical sampling (collection of spectra) results in anomalies. These may be based in environmental effects such as temperature or in instrumentation related issues such as applied pressure to the sampling site. Small sampling errors may result in spectra that are not representative of the desired sampled region. These unrepresentative spectra often greatly confound subsequent analysis. A simple example is that if you mean center a data set and utilize in the calculation of the mean an extreme outlier, then the mean is not ultimately subtracted. For another example, for analyses that utilize a multivariate model such as PLS or PCR spectral outliers greatly confound multivariate model generation and/or subsequent analysis. Hence, the purpose of outlier detection is to remove samples that confound model generation and/or maintenance. Separately, outlier detection is critical so that unrepresentative sample spectra are not converted into inaccurate predicted glucose concentrations but are rather reported as bad measurements.

As indicated in FIG. 3, the necessity for outlier detection, and the form of an outlier detection procedure are dependent on the sampling technology employed. However, in the preferred embodiment outlier detection is performed by comparing the preprocessed and transformed tissue measurement z to the members of the basis set through a distance metric or measure of similarity. Preferably one of the following metrics is used to determine a measure of similarity: Euclidean distance, the Mahalanobis distance, or the correlation coefficient. When the tissue measurement is no longer similar to the members of the basis set the interference has changed and a new basis set is collected. For example, when the basis set has one member that has been preprocessed, subsequent tissue members are compared with the basis set through the calculation of the correlation coefficient. If repeated tissue memberships have a correlation coefficient when compared to the basis set less than 0.98 the basis set is re-collected to represent the new tissue state.

Alternately, the detection of an invalid basis set is achieved by monitoring key optical properties of the sampled tissue that are reflected in select spectral features and determining if the variation in the features exceeds that from the calibration set or other previously established limits. Methods such as Principal Component Analysis (PCA) and Linear Discriminate Analysis (LDA) are used to define sample rejection criteria and set detection limits. Once it is determined that a new template is needed, the user collects N (N being greater than or equal to one) spectral samples and M (being greater than or equal to one) direct measurements of the desired biological constituent(s). Sample selection techniques described subsequently is applied to determine the subset of samples that will be used in computing the new tissue template.

Bias Adjustment

The correction of interference through a basis set leads to a bias in the measurement that causes a bias correction to be beneficial to both the calibration reference values and the analyte estimates. The bias adjustment is associated with each tissue basis set and is determined by comparing an analyte measurement with a known value. Specifically, the bias adjustment is set equal to the difference between an analyte measurement and the known property value according to:

$$b = y - \hat{y}; \tag{8}$$

where $\hat{y}$ is the noninvasive analyte measurement and y is the reference analyte value. When more than one pair of noninvasive analyte measurements and reference analyte values are available, then b is taken as the mean difference of all pairs. In the preferred embodiment, a reference analyte value is collected at the same time as the basis set and b=y.

During calibration, the reference property values are adjusted prior to the calculation of the calibration model by subtracting an analyte value associated with the tissue template measurement from each reference property value. In the preferred embodiment, the analyte value is calculated as the average of the reference property values associated with each member of the basis set.

Exemplary Application of the Invention

A data set was collected on five individuals with diabetes who participated in a clinical study involving the manipulation of blood glucose levels through carbohydrate ingestion and insulin administration. As part of the clinical protocol each subject participated in approximately three to four visits with each visit lasting approximately 8 hours and occurring at a minimum of four days apart. At the beginning of each visit a probe placement guide was attached to the tissue site in which future samples for that visit were to be collected. Spectral samples were collected by aligning the fiber optic probe from the near-infrared spectrometer with the aperture of the probe placement guide and inserting the fiber probe into the guide aperture by lowering the sample toward the probe. A reference blood glucose concentration was collected with each spectral sample and samples were collected approximately 15 minutes apart.

Figure 4:
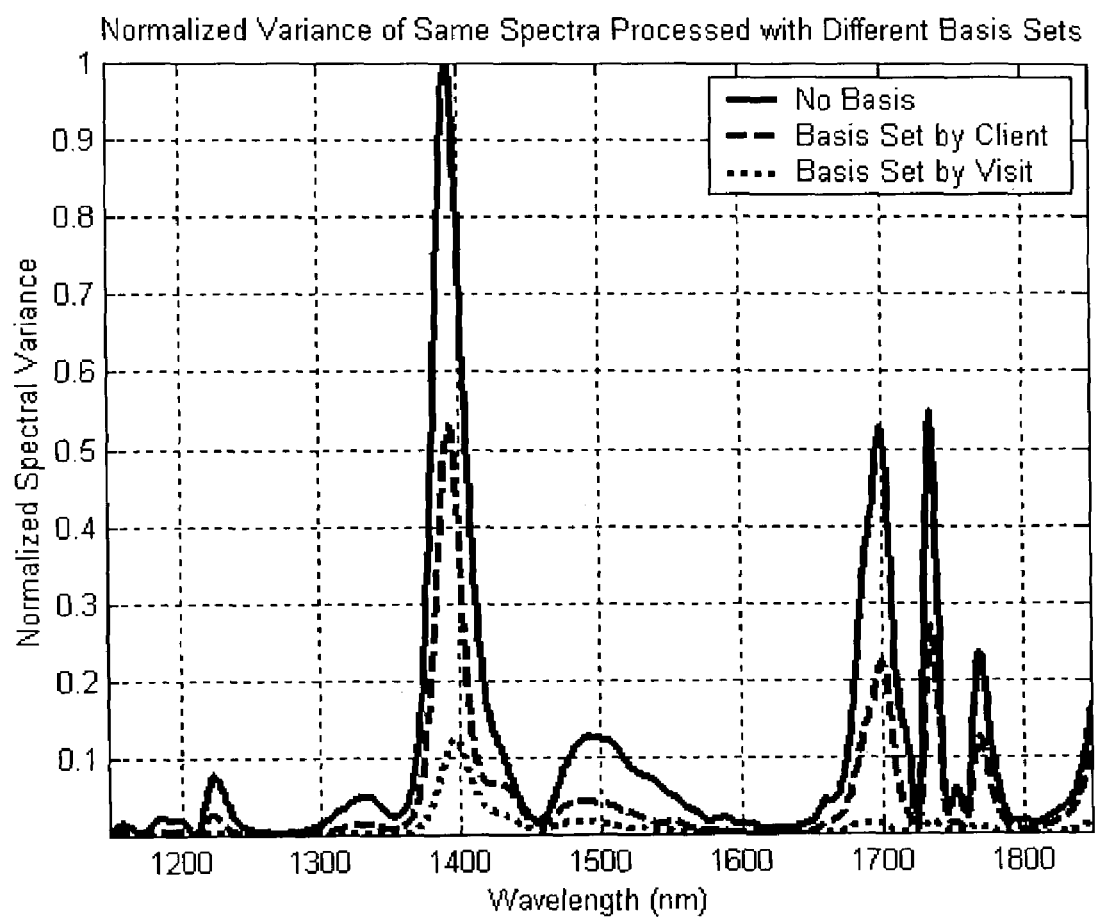
FIG. 4 is a plot of spectral variance of multi-individual, multi-day data set processed using three different basis sets.
Figure 5:
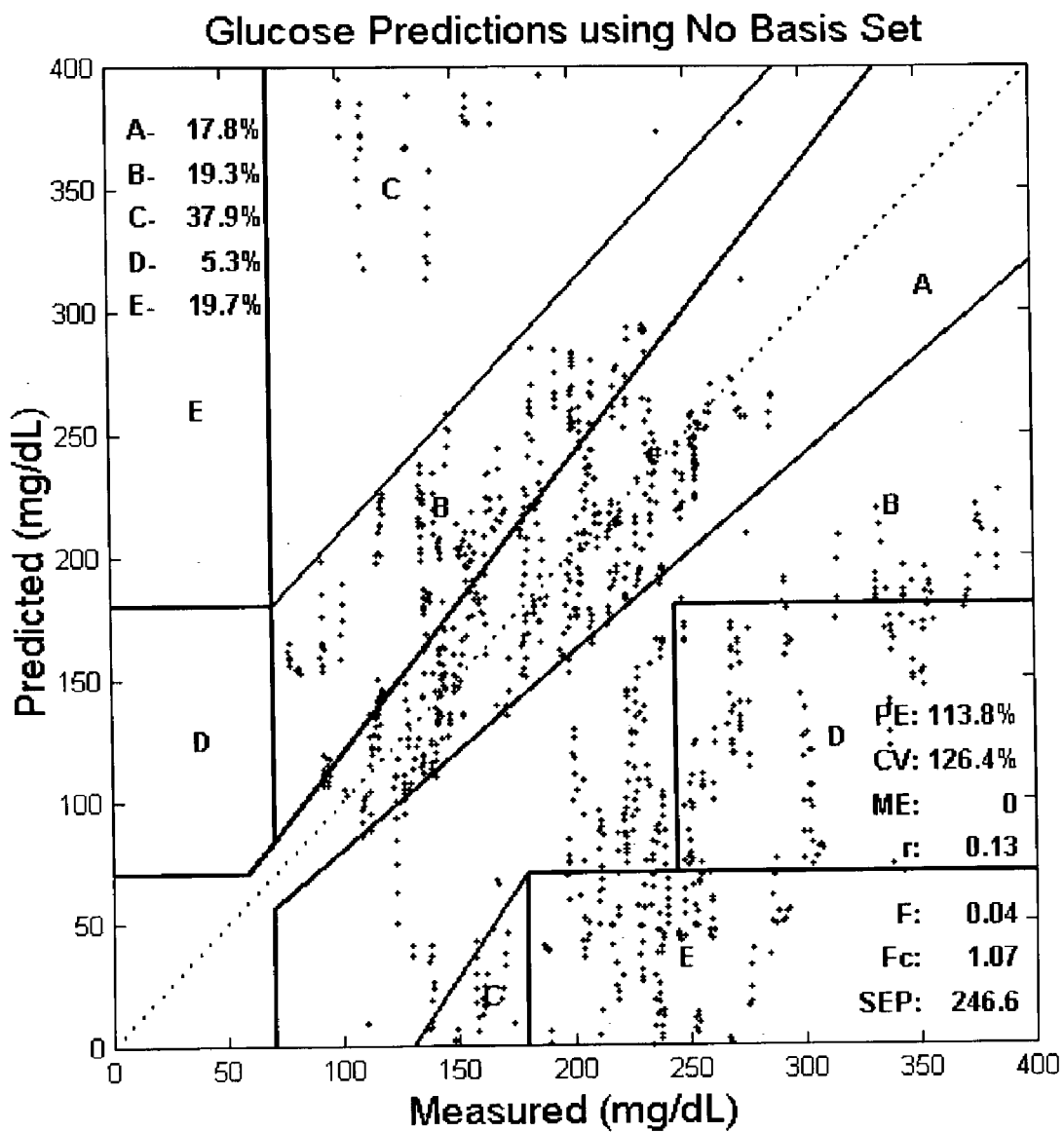
FIG. 5 is a Clarke-Error grid of glucose predictions using data that was processed using no basis set prior to application of a multivariable model.
Figure 6:
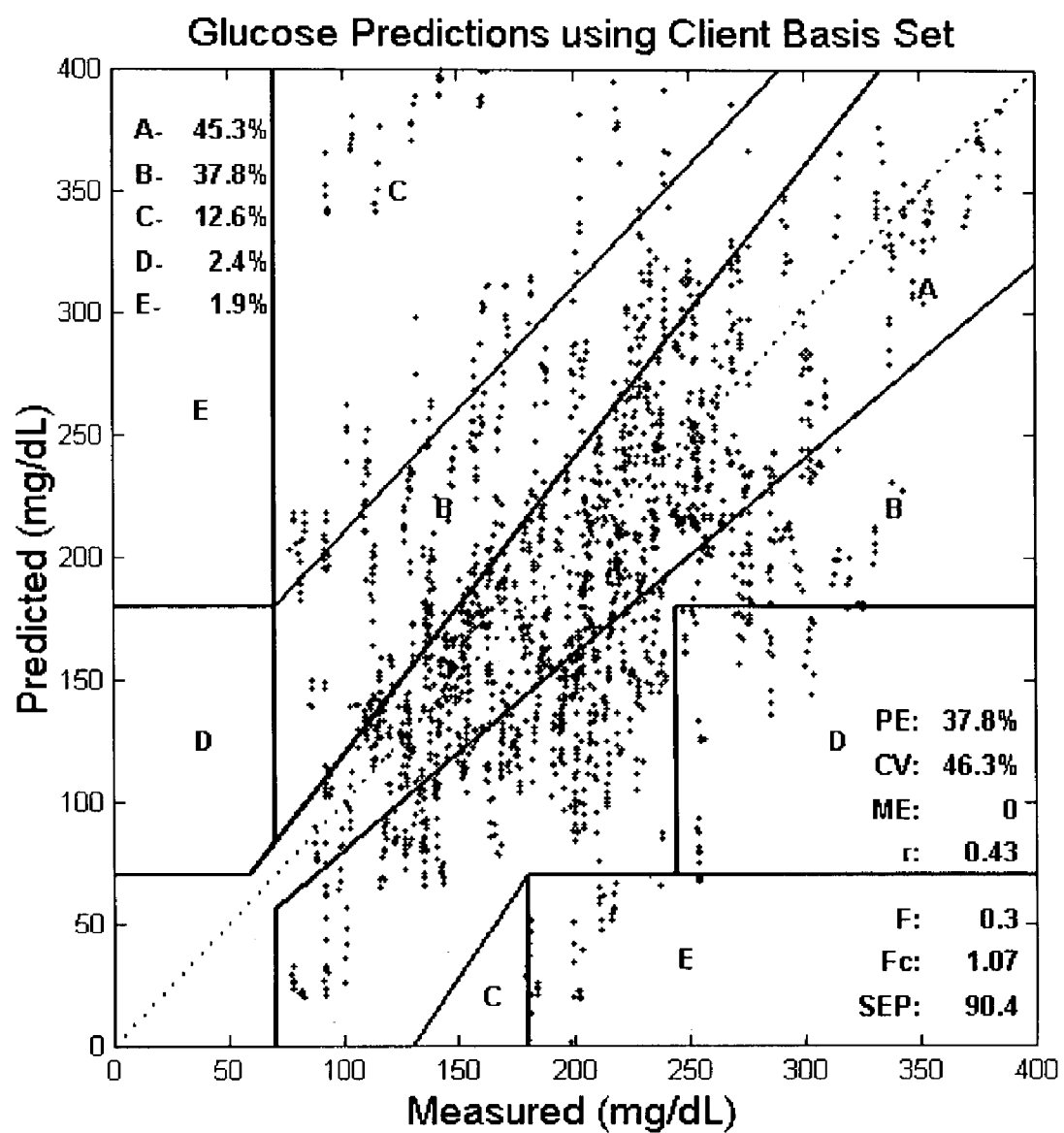
FIG. 6 is a Clarke-Error grid of glucose predictions using data that was processed using a basis set that was created for each subject.
Figure 7:
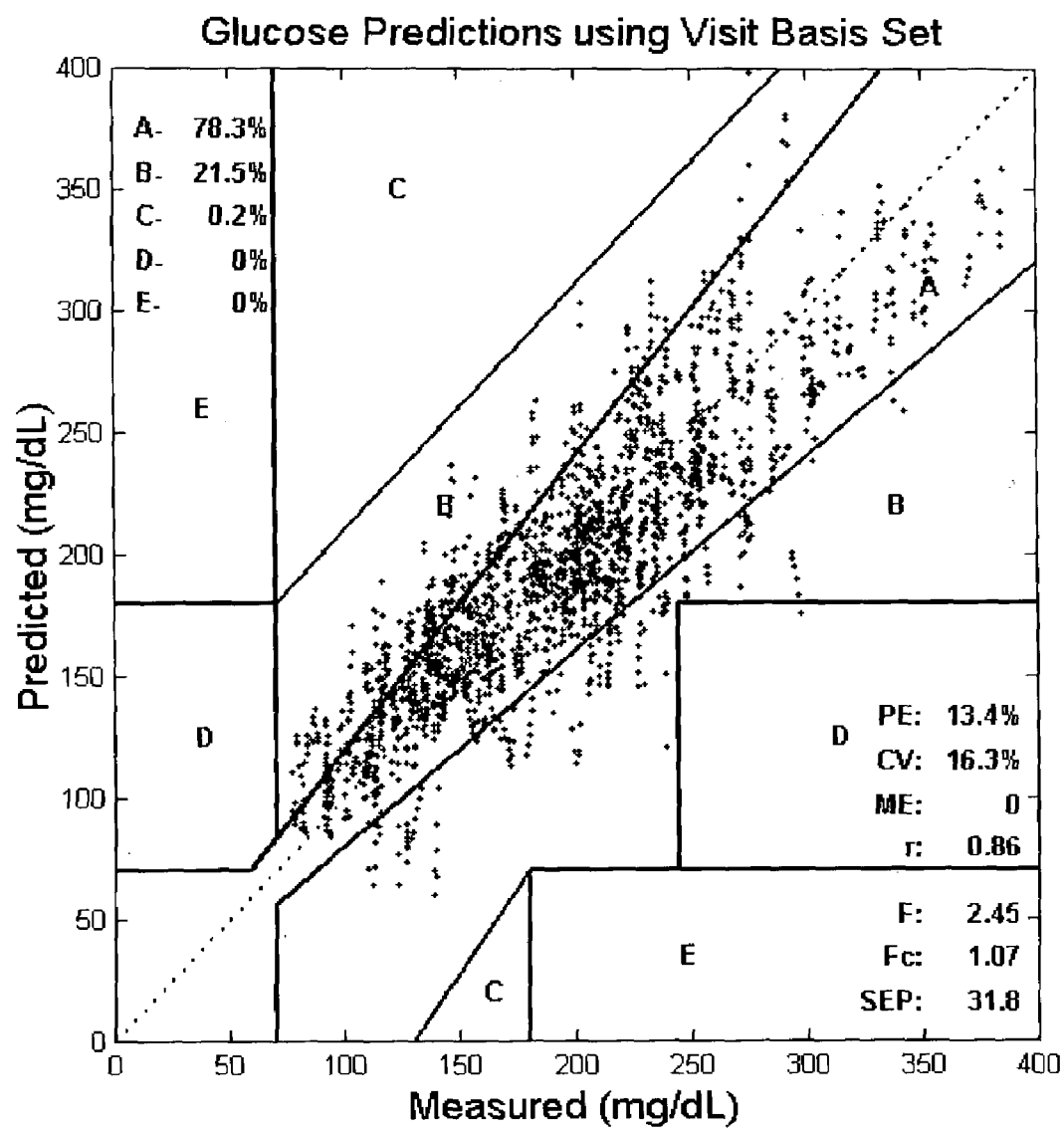
FIG. 7 is a Clarke-Error grid of glucose predictions using data that was processed using a basis set that was created for each visit or day.

The collected spectral measurements were preprocessed using no basis set, a client specific basis set in which a subset of data from each individual was used to process their own respected data, and a visit specific basis set according to the preferred embodiment of the invention in which a subset of data from each visit was used to process their respected visits. The spectral variance associated with the three preprocessed and transformed data sets were computed at each wavelength and are plotted in FIG. 4. The overall variance across all wavelengths was reduced using the client basis set and was further reduced using the visit specific basis set. The client specific basis set successfully reduces the patient-to-patient interference but fails to address the key problem related to sample heterogeneity and complexity and physiological and chemical variation related to the dynamic nature of the tissue that occurs over time. Application of the visit specific basis set localizes the collected measurements with respect to the sampled tissue site and time which attenuates major interferences caused by tissue heterogeneity and physiological variation. A standardized multivariable glucose calibration model that was previously developed using the process disclosed in the invention was applied to preprocessed and transformed data sets to determine the impact of each method on glucose prediction. FIGS. 5 and 6 contain the independent glucose predictions on a Clarke-Error grid obtained from the data corrected using no basis set and a client specific basis set, respectively. FIG. 7 contains the independent predictions from the data processed using the visit specific basis set that was computed using the method described in the preferred embodiment. The predictions obtained by applying no basis set and a client basis set exposed the existence of different clusters in the predictions representing the variability of the optically sampled tissue between individuals and within individuals on different visits. The distances between clusters in the Clarke-Error grid were reduced but not effectively removed when applying a client basis set to the data. Application of the visit specific basis revealed no inherent clusters in the glucose predictions and significantly improved prediction accuracy between individuals and within an individual between visits. This illustrates the effectiveness of the disclosed method versus the previous methods in effectively compensating for interferences related to tissue heterogeneity, patient-to-patient variation, instrument related variation, and physiological variation through time.

The preferred embodiments disclosed herein have been described and illustrated by way of example only, and not by way of limitation. Other modifications and variations to the invention will be apparent to those skilled in the art from the foregoing detailed disclosure. While only certain embodiments of the invention have been specifically described herein, it will be apparent that numerous modifications may be made thereto without departing from the spirit and scope of the invention.

Accordingly, the invention should only be limited by the Claims included below.

What is claimed is:

1. A method for noninvasively measuring a target analyte in a body using spectroscopic analysis, comprising the steps of:
   collecting a sample measurement which is a response signal from said body to which a probing signal is applied;
   transforming said sample measurement by applying a tissue basis set to said sample measurement, said tissue basis set including at least one interfering component, wherein any interference in said sample measurement corresponding to said at least one interfering component in said tissue basis set is removed;
   calibrating said transformed sample measurement by applying a calibration model, wherein said calibration model is determined from a calibration set of exemplary paired data points; and
   determining a noninvasive measurement of said target analyte.

2. The method of claim 1, wherein said collecting step further comprises the step of:
   preprocessing said collected sample measurement to attenuate noises and enhance a net analytical signal representative of said target analyte.

3. The method of claim 2, wherein said preprocessing step comprises any of: filtering, averaging, derivative calculation, multiplicative scatter correction, smoothing, and normalization.

4. The method of claim 1, wherein said at least one interfering component results from any of: sample heterogeneity, patient-to-patient variation, instrument related variation, and physiological variation.

5. The method of claim 1, wherein said tissue basis set is a set of measurements that are collected at various sample sites on a particular patient associated with a particular time period and a particular instrument.

6. The method of claim 5, wherein said tissue basis set is generated with the first n measurements of a day, wherein $n \geq 1$.

7. The method of claim 5, wherein said basis set is generated with the last n measurements prior to a current sample, wherein $n \geq 1$.

8. The method of claim 5, wherein said basis set is generated with a moving window of samples.

9. The method of claim 1, wherein said tissue basis set is determined for each patient, visit, and instrument by preprocessing each sample measurement and then calculating the mean of all preprocessed sample measurements associated with said each patient, visit, and instrument.

10. The method of claim 1, wherein said tissue basis set is determined based on a process of optimizing sample selection.

11. The method of claim 10, wherein said process of optimizing sample selection comprises the step of:
   calculating an estimate mean of a data set targeted for said tissue basis set.

12. The method of claim 11, wherein said estimate mean is determined by excluding the highest and lowest approximate 25% of values at each wavelength or variable prior to averaging.

13. The method of claim 10, wherein said process of optimizing sample selection comprises the steps of:
   performing a principal component analysis (PCA); and
   removing any sample that contains high leverage with respect to a relevant sample population.

14. The method of claim 13, wherein said process of optimizing sample selection comprises the step of:
   removing any sample that, when it is left out, may result in a drop in covariance greater than a preset limit.

15. The method of claim 13, wherein said process of optimizing sample selection comprises the step of:
   performing a T-squared or a Q-test of the principal component scores used in said principal component analysis (PCA).

16. The method of claim 13, wherein said process of optimizing sample selection comprises the step of:
   excluding any sample that exceeds a defined confidence interval.

17. The method of claim 10, wherein said process of optimizing sample selection comprises the step of:
   converting a number of spectroscopic factors into a single set of property values which is used to determine an optical state of a sample encountered; and
   excluding any sample whose optical state is inconsistent with a predefined optical state.

18. The method of claim 17, wherein said number of spectroscopic factors contain information related to any of: fat, water, protein, surface reflectance, and probe-to-surface contact.

19. The method of claim 10, wherein said process of optimizing sample selection comprises the steps of:
   propagating collected spectral measurements through a rudimentary predictive model; and
   comparing a set of resulting analyte estimates to spectral features that are related to essential optical characteristics of a sample encountered.

20. The method of claim 1, wherein said transforming step is performed according to $$z = f(x, S, P)$$

wherein z is said transformed sample measurement, S is said tissue basis set, P is a set of weights or normalization parameters, and $f(.)$ is a function that is used to attenuate the interference represented by S that is contained in x.

21. The method of claim 20, wherein said transforming step comprises a calculation selected from any of: subtraction, weighted subtraction, division, deconvolution, multiplicative scatter correction, and rotation.

22. The method of claim 1, wherein said transforming step is performed according to $$z = x - (c^T S + d)$$

wherein $c \in \Re^{1 \times P}$ is used to weight each member of said tissue basis set to optimally reduce the interference in x, $d \in \Re^{1 \times N}$ is an intercept adjustment, and coefficients c and d are either preset or determined through multiple linear regression.

23. The method of claim 1, wherein each of said paired data points comprise a transformed measurement and an associated reference analyte value.

24. The method of claim 1, further comprising the step of:
   making an offset adjustment on said calibrated measurement.

25. The method of claim 1, wherein said calibration model is given by $$\hat{y} = f(z) + b;$$

wherein $\hat{y}$ is an estimated concentration of said target analyte, $z \in \Re^{1 \times N}$ is said transformed sample measurement, $f: \Re^N \to \Re^1$ is a model used to measure said target analyte based on said transformed sample measurement, and b is an offset adjustment for said target analyte measurement.

26. The method of claim 1, wherein said calibration model is given by $$\hat{y}=zF+b;$$

wherein $\hat{y}$ is an estimated concentration of said target analyte, $z \in \mathfrak{R}^{1 \times N}$ is said transformed sample measurement, $F \in \mathfrak{R}^{N \times 1}$ and b is an offset adjustment for said analyte measurement.

27. The method of claim 1, further comprising the step of:
making a bias adjustment on said calibrated measurement, said bias adjustment being associated with each applied tissue basis set and is determined by comparing an analyte measurement with a reference analyte value.

28. The method of claim 27, wherein said bias adjustment is set equal to the difference between said analyte measurement and said reference analyte value.

29. The method of claim 28, wherein said reference analyte value is collected at the same time as said tissue basis set, and said bias adjustment is set equal to said reference analyte value.

30. The method of claim 28, wherein when more than one pair of analyte measurements and reference analyte values are available, said bias adjustment is taken as the mean difference of all pairs.

31. The method of claim 30, wherein said noninvasive measurement of said target analyte is calculated as the average of said reference analyte values associated with each member of said tissue basis set.

32. The method of claim 1, further comprising the step of:
performing an outlier detection by comparing said transformed sample measurement to the members of said tissue basis set through a distance metric or measure of similarity;
wherein when said transformed sample measurement is no longer similar to the members of said tissue basis set, a new tissue basis set is determined.

33. The method of claim 1, wherein said noninvasive measurement is displayed digitally or graphically or both.

34. An apparatus for noninvasively measuring a target analyte in a body using spectroscopic analysis, comprising:
means for transmitting a probe signal into said body;
means for detecting said signal responded from said body; and
means for converting said detected signal into a sample measurement of said analyte;
wherein said means for converting is operable to:
transform said sample measurement by applying a tissue basis set thereto, said tissue basis set including at least one interfering component, wherein any interference in said sample measurement corresponding to said at least one interfering component in said tissue basis set is removed;
apply a calibration model to said transformed sample measurement, wherein said calibration model is determined from a calibration set of exemplary paired data points; and
display a noninvasive measurement of said target analyte.

35. The apparatus of claim 34, wherein said means for converting further comprises:
means for preprocessing said detected signal to attenuate noises and enhance a net analytical signal representative of said target analyte.

36. The apparatus of claim 35, wherein said means for preprocessing comprises any of: filtering, averaging, calculating a derivative, performing multiplicative scatter correction, smoothing, and normalizing.

37. The apparatus of claim 34, wherein said at least one interfering component results from any of: sample heterogeneity, patient-to-patient variation, instrument related variation, and physiological variation.

38. The apparatus of claim 34, wherein said tissue basis set is a set of measurements that are collected at various sample sites on a particular patient associated with a particular time period and a particular instrument.

39. The apparatus of claim 38, wherein said tissue basis set is generated with the first n measurements of a day, wherein $n \geq 1$.

40. The apparatus of claim 38, wherein said basis set is generated with the last n measurements prior to a current sample, wherein $n \geq 1$.

41. The apparatus of claim 38, wherein said basis set is generated with a moving window of samples.

42. The apparatus of claim 34, wherein said tissue basis set is determined for each patient, visit, and instrument by preprocessing each sample measurement and then calculating the mean of all preprocessed sample measurements associated with said each patient, visit, and instrument.

43. The apparatus of claim 34, wherein said tissue basis set is determined based on a process of optimizing sample selection.

44. The apparatus of claim 43, wherein said process of optimizing sample selection comprises the operation of:
calculating an estimate mean of a data set targeted for said tissue basis set.

45. The apparatus of claim 44, wherein said estimate mean is determined by excluding the highest and lowest approximate 25% of values at each wavelength or variable prior to averaging.

46. The apparatus of claim 43, wherein said process of optimizing sample selection comprises the operations of:
performing a principal component analysis (PCA); and
removing any sample that contains high leverage with respect to a relevant sample population.

47. The apparatus of claim 46, wherein said process of optimizing sample selection comprises the operation of:
removing any sample that, when it is left out, may result in a drop in covariance greater than a preset limit.

48. The apparatus of claim 46, wherein said process of optimizing sample selection comprises the operation of:
performing a T-squared or a Q-test of the principal component scores used in said principal component analysis (PCA).

49. The apparatus of claim 46, wherein said process of optimizing sample selection comprises the operation of:
excluding any sample that exceeds a defined confidence interval.

50. The apparatus of claim 43, wherein said process of optimizing sample selection comprises the operation of:
converting a number of spectroscopic factors into a single set of property values which is used to determine an optical state of a sample encountered; and
excluding any sample whose optical state is inconsistent with a predefined optical state.

51. The apparatus of claim 50, wherein said number of spectroscopic factors contain information related to any of: fat, water, protein, surface reflectance, and probe-to-surface contact.

52. The apparatus of claim 43, wherein said process of optimizing sample selection comprises the operations of:

propagating collected spectral measurements through a rudimentary predictive model; and comparing a set of resulting analyte estimates to spectral features that are related to essential optical characteristics of a sample encountered.

53. The apparatus of claim 34, wherein said transformation is performed according to $$z = f(x, S, P)$$

wherein z is said transformed sample measurement, S is said tissue basis set, P is a set of weights or normalization parameters, and $f(.)$ is a function that is used to attenuate the interference represented by S that is contained in x.

54. The apparatus of claim 53, wherein said transformation comprises a calculation selected from any of: subtraction, weighted subtraction, division, deconvolution, multiplicative scatter correction, and rotation.

55. The apparatus of claim 34, wherein said transformation is performed according to $$z = x - (c^T S + d)$$

wherein $c \in \Re^{1 \times P}$ is used to weight each member of said tissue basis set to optimally reduce the interference in x, $d \in \Re^{1 \times N}$ is an intercept adjustment, and coefficients c and d are either preset or determined through multiple linear regression.

56. The apparatus of claim 34, wherein each of said paired data points comprise a transformed measurement and an associated reference analyte value.

57. The apparatus of claim 34, further comprising:
means for making an offset adjustment on said calibrated measurement.

58. The apparatus of claim 34, wherein said calibration model is given by $$\hat{y} = f(z) + b;$$

wherein $\hat{y}$ is an estimated concentration of said target analyte, $z \in \Re^{1 \times N}$ is said transformed sample measurement, $f: \Re^N \to \Re^1$ is a model used to measure said target analyte based on said transformed sample measurement, and b is an offset adjustment for said target analyte measurement.

59. The apparatus of claim 34, wherein said calibration model is given by $$\hat{y} = zF + b;$$

wherein $\hat{y}$ is an estimated concentration of said target analyte, $z \in \Re^{1 \times N}$ is said transformed sample measurement, $F \in \Re^{N \times 1}$ and b is an offset adjustment for said analyte measurement.

60. The apparatus of claim 34, further comprising:
means for making a bias adjustment on said calibrated measurement, said bias adjustment being associated with each applied tissue basis set and is determined by comparing an analyte measurement with a reference analyte value.

61. The apparatus of claim 60, wherein said bias adjustment is set equal to the difference between said analyte measurement and said reference analyte value.

62. The apparatus of claim 61, wherein said reference analyte value is collected at the same time as said tissue basis set, and said bias adjustment is set equal to said reference analyte value.

63. The apparatus of claim 62, wherein when more than one pair of analyte measurements and reference analyte values are available, said bias adjustment is taken as the mean difference of all pairs.

64. The apparatus of claim 63, wherein said noninvasive measurement of said target analyte is calculated as the average of said reference analyte values associated with each member of said tissue basis set.

65. The apparatus of claim 34, further comprising:
means for performing an outlier detection by comparing said transformed sample measurement to the members of said tissue basis set through a distance metric or measure of similarity;
wherein when said transformed sample measurement is no longer similar to the members of said tissue basis set, a new tissue basis set is determined.

66. The apparatus of claim 34, wherein said noninvasive measurement is displayed digitally or graphically or both.

67. A computer usable medium containing instructions in computer readable form for carrying out a method for noninvasively measuring a target analyte in a body using spectroscopic analysis, said method comprising the steps of:
collecting a sample measurement which is a response signal from said body to which a probing signal is applied;
transforming said sample measurement by applying a tissue basis set to said sample measurement, said tissue basis set including at least one interfering component, wherein any interference in said sample measurement corresponding to said at least one interfering component in said tissue basis set is removed;
calibrating said transformed sample measurement by applying a calibration model, wherein said calibration model is determined from a calibration set of exemplary paired data points; and
determining a noninvasive measurement of said target analyte.

68. The computer usable medium of claim 67, wherein said collecting step further comprises the step of:
preprocessing said collected sample measurement to attenuate noises and enhance a net analytical signal representative of said target analyte.

69. The computer usable medium of claim 68, wherein said preprocessing step comprises any of: filtering, averaging, derivative calculation, multiplicative scatter correction, smoothing, and normalization.

70. The computer usable medium of claim 67, wherein said at least one interfering component results from any of: sample heterogeneity, patient-to-patient variation, instrument related variation, and physiological variation.

71. The computer usable medium of claim 67, wherein said tissue basis set is a set of measurements that are collected at various sample sites on a particular patient associated with a particular time period and a particular instrument.

72. The computer usable medium of claim 71, wherein said basis set is generated with the first n measurements of a day, wherein $n \geq 1$.

73. The computer usable medium of claim 71, wherein said basis set is generated with the last n measurements prior to a current sample, wherein $n \geq 1$.

74. The computer usable medium of claim 71, wherein said basis set is generated with a moving window of samples.

75. The computer usable medium of claim 67, wherein said tissue basis set is determined for each patient, visit, and instrument by preprocessing each sample measurement and then calculating the mean of all preprocessed sample measurements associated with said each patient, visit, and instrument.

76. The computer usable medium of claim 67, wherein said tissue basis set is determined based on a process of optimizing sample selection.

77. The computer usable medium of claim 67, wherein said process of optimizing sample selection comprises the step of:
   calculating an estimate mean of a data set targeted for said tissue basis set.

78. The computer usable medium of claim 77, wherein said estimate mean is determined by excluding the highest and lowest approximate 25% of values at each wavelength or variable prior to averaging.

79. The computer usable medium of claim 76, wherein said process of optimizing sample selection comprises the steps of:
   performing a principal component analysis (PCA); and
   removing any sample that contains high leverage with respect to a relevant sample population.

80. The computer usable medium of claim 79, wherein said process of optimizing sample selection comprises the step of:
   removing any sample that, when it is left out, may result in a drop in covariance greater than a preset limit.

81. The computer usable medium of claim 79, wherein said process of optimizing sample selection comprises the step of:
   performing a T-squared or a Q-test of the principal component scores used in said principal component analysis (PCA).

82. The computer usable medium of claim 79, wherein said process of optimizing sample selection comprises the step of:
   excluding any sample that exceeds a defined confidence interval.

83. The computer usable medium of claim 76, wherein said process of optimizing sample selection comprises the step of:
   converting a number of spectroscopic factors into a single set of property values which is used to determine an optical state of a sample encountered; and
   excluding any sample whose optical state is inconsistent with a predefined optical state.

84. The computer usable medium of claim 83, wherein said number of spectroscopic factors contain information related to any of: fat, water, protein, surface reflectance, and probe-to-surface contact.

85. The computer usable medium of claim 76, wherein said process of optimizing sample selection comprises the steps of:
   propagating collected spectral measurements through a rudimentary predictive model; and
   comparing a set of resulting analyte estimates to spectral features that are related to essential optical characteristics of a sample encountered.

86. The computer usable medium of claim 67, wherein said transforming step is performed according to $$z = f(x, S, P)$$

wherein z is said transformed sample measurement, S is said tissue basis set, P is a set of weights or normalization parameters, and $f(.)$ is a function that is used to attenuate the interference represented by S that is contained in x.

87. The computer usable medium of claim 86, wherein said transforming step comprises a calculation selected from any of: subtraction, weighted subtraction, division, deconvolution, multiplicative scatter correction, and rotation.

88. The computer usable medium of claim 67, wherein said transforming step is performed according to $$z = x - (c^T S + d)$$

wherein $c \in \Re^{1 \times P}$ is used to weight each member of said tissue basis set to optimally reduce the interference in x, $d \in \Re^{1 \times N}$ is an intercept adjustment, and coefficients c and d are either preset or determined through multiple linear regression.

89. The computer usable medium of claim 67, wherein each of said paired data points comprise a transformed measurement and an associated reference analyte value.

90. The computer usable medium of claim 67, wherein said method further comprises the step of:
   making an offset adjustment on said calibrated measurement.

91. The computer usable medium of claim 67, wherein said calibration model is given by $$\hat{y} = f(z) + b;$$

wherein $\hat{y}$ is an estimated concentration of said target analyte, $z \in \Re^{1 \times N}$ is said transformed sample measurement, $f: \Re^N \to \Re^1$ is a model used to measure said target analyte based on said transformed sample measurement, and b is an offset adjustment for said target analyte measurement.

92. The computer usable medium of claim 67, wherein said calibration model is given by $$\hat{y} = zF + b;$$

wherein $\hat{y}$ is an estimated concentration of said target analyte, $z \in \Re^{1 \times N}$ is said transformed sample measurement, $F \in \Re^{N \times 1}$ and b is an offset adjustment for said analyte measurement.

93. The computer usable medium of claim 67, wherein said method further comprises the step of:
   making a bias adjustment on said calibrated measurement, said bias adjustment being associated with each applied tissue basis set and is determined by comparing an analyte measurement with a reference analyte value.

94. The computer usable medium of claim 93, wherein said bias adjustment is set equal to the difference between said analyte measurement and said reference analyte value.

95. The computer usable medium of claim 94, wherein said reference analyte value is collected at the same time as said tissue basis set, and said bias adjustment is set equal to said reference analyte value.

96. The computer usable medium of claim 94, wherein when more than one pair of analyte measurements and reference analyte values are available, said bias adjustment is taken as the mean difference of all pairs.

97. The computer usable medium of claim 96, wherein said noninvasive measurement of said target analyte is calculated as the average of said reference analyte values associated with each member of said tissue basis set.

98. The computer usable medium of claim 67, wherein said method further comprises the step of:
   performing an outlier detection by comparing said transformed sample measurement to the members of said tissue basis set through a distance metric or measure of similarity;

wherein when said transformed sample measurement is no longer similar to the members of said tissue basis set, a new tissue basis set is determined.

99. The computer usable medium of claim 67, wherein said noninvasive measurement is displayed digitally or graphically or both.

100. A method for noninvasively measuring a target analyte in a body using spectroscopic analysis, comprising the steps of:
   collecting a sample measurement which is a response signal from said body to which a probing signal is applied;
   transforming said sample measurement by applying a basis set to said sample measurement, said basis set including at least one interfering component, wherein at least one interference in said sample measurement corresponding to said at least one interfering component in said basis set is removed;
   calibrating said transformed sample measurement by applying a calibration model,
   making a bias adjustment on said calibrated measurement, said bias adjustment being associated with each applied basis set and is determined by comparing an analyte measurement with a reference analyte value; and
   determining a noninvasive measurement of said target analyte.

101. A method for noninvasively measuring a target analyte in a body using spectroscopic analysis, comprising the steps of:
   collecting a sample measurement which is a response signal from said body to which a probing signal is applied;
   transforming said sample measurement by applying a basis set to said sample measurement said basis set including at least one interfering component, wherein any interference in said sample measurement corresponding to said at least one interfering component in said basis set is removed, wherein said basis set is determined for each patient and instrument by preprocessing each sample measurement, and then calculating a mathematical representation of the preprocessed sample measurements associated with said each patient and instrument;
   calibrating said transformed sample measurement by applying a calibration model; and
   determining a noninvasive measurement of said target analyte.

102. The method of claim 101, wherein transforming includes any of:
   weighted subtraction;
   division;
   deconvolution;
   rotation; and
   multiplicative scatter correction.

103. The method of claim 101, wherein said basis set is determined for a visit.

104. The method of claim 101, wherein said basis set is determined for a guide placement.

105. An apparatus for noninvasively measuring a target analyte in a body using a spectroscopic analysis, comprising:
   means for transmitting a probe signal into said body;
   means for detecting said signal responded from said body; and
   means for converting said detected signal into a sample measurement of said analyte;
   wherein said means for converting is operative to:
   transform said sample measurement by applying a basis set thereto, said basis set including at least one interfering component, wherein said basis set is determined for each patient and instrument by preprocessing each sample measurement and then calculating a mathematical representation of the preprocessed sample measurements associated with said each patient and instrument, wherein at least one interference in said sample measurement corresponding to said at least one interfering component in said basis set is removed;
   apply a calibration model to said transformed sample measurement; and
   display a noninvasive measurement of said target analyte.

106. The method of claim 101, wherein transforming includes any of:
   weighted subtraction;
   division;
   deconvolution;
   rotation; and
   multiplicative scatter correction.

107. An apparatus for noninvasively measuring a target analyte in a body using spectroscopic analysis, comprising;
   means for transmitting a probe signal into said body;
   means for detecting said signal responded from said body;
   means for converting said detected signal into a sample measurement of said analyte;
   wherein said means for converting is operative to:
   transform said sample measurement by applying a basis set thereto, said basis set including at least one interfering component, wherein any interference in said sample measurement corresponding to said at least one interfering component in said basis set is removed;
   apply a calibration model to said transformed sample measurement; and
   make a bias adjustment on said calibration model, said bias adjustment being associated with each applied basis set and is determined by comparing an analyte measurement with a reference analyte value; and
   display a noninvasive measurement of said target analyte.

* * * * *